United States Patent
Sander et al.

(10) Patent No.: US 7,048,762 B1
(45) Date of Patent: May 23, 2006

(54) ELONGATED CORTICAL BONE IMPLANT

(75) Inventors: Tom Sander, Alachua, FL (US); Kevin C. Carter, Alachua, FL (US)

(73) Assignee: Regeneration Technologies, Inc., Alachua, FL (US)

( * ) Notice: Subject to any disclaimer, the term of this patent is extended or adjusted under 35 U.S.C. 154(b) by 0 days.

(21) Appl. No.: 09/701,933

(22) PCT Filed: Aug. 27, 1998

(86) PCT No.: PCT/US98/17769

§ 371 (c)(1),
(2), (4) Date: Aug. 20, 2001

(87) PCT Pub. No.: WO99/09914

PCT Pub. Date: Mar. 4, 1999

Related U.S. Application Data

(63) Continuation-in-part of application No. 08/920,630, filed on Aug. 27, 1997, now abandoned.

(51) Int. Cl.
*A61F 2/44* (2006.01)

(52) U.S. Cl. .................................................. 623/17.11
(58) Field of Classification Search ............ 623/16.11, 623/17.11, 17.16
See application file for complete search history.

(56) References Cited

U.S. PATENT DOCUMENTS

| | | | |
|---|---|---|---|
| 4,349,921 A | * | 9/1982 | Kuntz .................. 623/17.16 |
| 4,904,261 A | * | 2/1990 | Dove et al. ............... 623/17 |
| 4,950,296 A | | 8/1990 | McIntyre |
| 5,112,354 A | * | 5/1992 | Sires ........................ 623/16 |
| 5,192,327 A | * | 3/1993 | Brantigan .................. 623/17 |
| 5,306,307 A | | 4/1994 | Senter et al. |
| 5,306,309 A | | 4/1994 | Wagner et al. |
| 5,397,364 A | | 3/1995 | Kozak et al. |
| 5,522,899 A | | 6/1996 | Michelson |
| 5,609,635 A | | 3/1997 | Michelson |
| 5,645,598 A | * | 7/1997 | Brosnahan, III ............. 623/17 |
| 5,728,159 A | * | 3/1998 | Stroever et al. ............. 623/16 |

(Continued)

FOREIGN PATENT DOCUMENTS

WO   WO 98/17209   *   4/1998

OTHER PUBLICATIONS

Bailey, R.W., and Badgley, L.E. "Stabilization of the Cervical Spine by Anterior Fusion." J. Bone and Joint Surg. (1960) 42A: 565-594.

(Continued)

*Primary Examiner*—Bruce Snow
(74) *Attorney, Agent, or Firm*—Donald J. Pochopien; McAndrews, Held & Malloy

(57) ABSTRACT

An implant composed substantially of cortical bone is provided for use in cervical Smith-Robinson vertebral fusion procedures. The implant is derived from allograft or autograft cortical bone sources, is machined to form a symmetrically or asymmetrically shaped (e.g. a substantially "D"-shaped) implant having a canal running therethrough according to methods of this invention, and inserted into the space between adjacent cervical vertebrae to provide support and induce fusion of the adjacent vertebrae. Osteogenic, osteoinductive or osteoconductive materials may be packed into the canal of the implant to expedite vertebral fusion and to allow autologous bony ingrowth.

31 Claims, 22 Drawing Sheets

U.S. PATENT DOCUMENTS 5,989,289 A * 11/1999 Coates et al. ............ 623/17.16
6,033,438 A *  3/2000 Bianchi et al. ............... 623/17
6,258,125 B1   7/2001 Paul et al.
6,277,149 B1   8/2001 Boyle et al.
6,371,988 B1 * 4/2002 Pafford et al. ........... 623/17.11

OTHER PUBLICATIONS

Cloward, R.B. "The Anterior Approach for Removal of Ruptured Cervical Discs." J. Bone and Joint Surg. (1958) 15: 602-617.

Grooms et al. "Success of Surgery on the Anterior Cervical Spine: Smith-Robinson Technique vs. Internal Plates." Clinical Performance of Skeletal Prostheses (1996) L.L. Hench and J. Wilson Eds., Chapman & Hall.

Robinson, R.A. et al. "The Results of Anterior Interbody Fusion of the Cervical Spine." J. Bone and Joint Surg. (1962) 44A: 1569-1587.

Robinson, R.A. and Smith, G.W. "Anterolateral Cervical Disc Removal and Interbody Fusion for Cervical Disc Syndrome." Bull, John Hopkins Hosp. (1955) 96: 223-224.

Smith, G.W. and Robinson, R.A. "The Treatment of Certain Cervical-Spine Disorders by Anterior Removal of the Intervertebral Disc and Interbody Fusion." J. Bone and Joint Surg. (1958) 40A: 607-623.

White, A.A. III, and Hirsh, C. "An Experimental Study of the Immediate Load Bearing Capacity of Some Commonly Used Iliac Bone Grafts." Acta Orthop. Scandanav. (1972) 42: 482-490.

Whitecloud, T.S. III and Dunsker, S. "Anterior Cervical Spine Surgery, Principles and Techniques in Spine Surgery." Raven Press, N.Y. (1993).

Albee, "Bone Surgery with Machine Tools" Scientific American, 154(4): 178-181 (Apr. 1936).

* cited by examiner

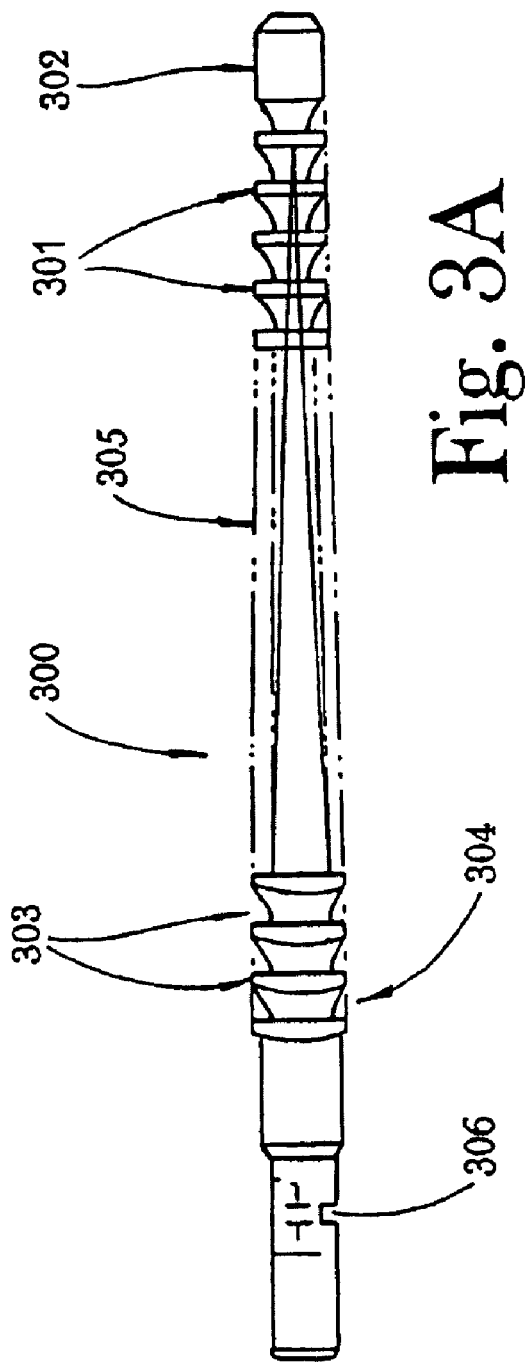
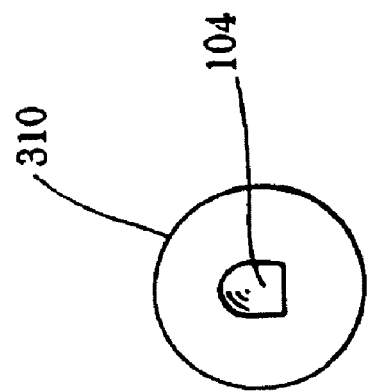
Fig. 3A
Fig. 3B

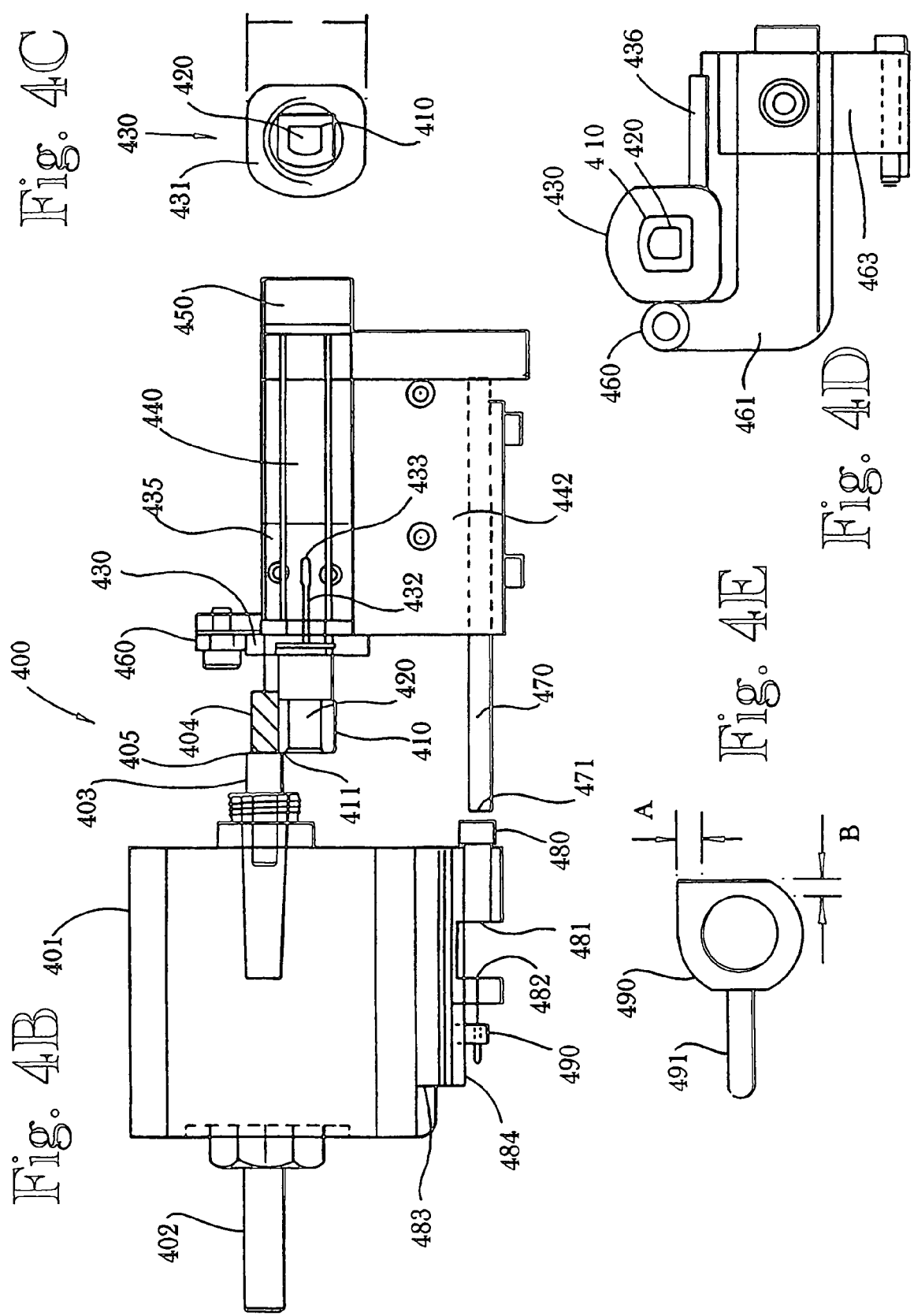

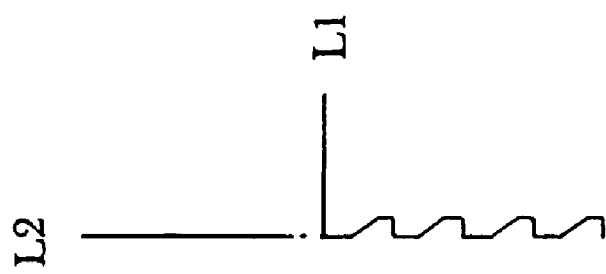
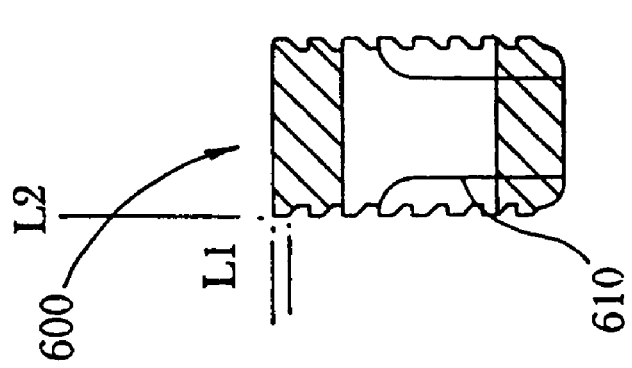
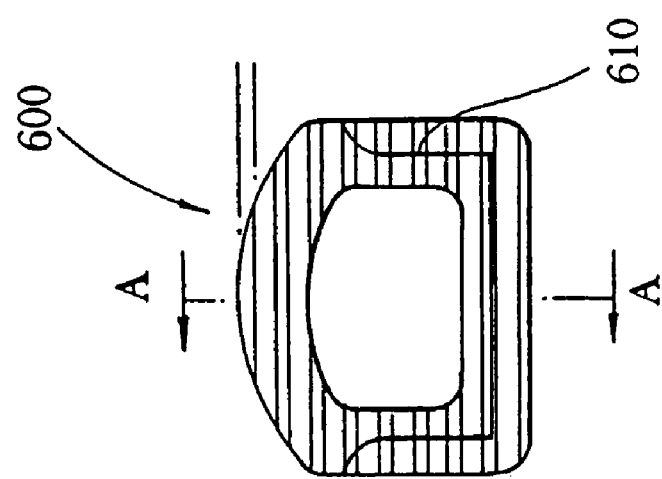
Fig. 6C
Fig. 6B
Fig. 6A

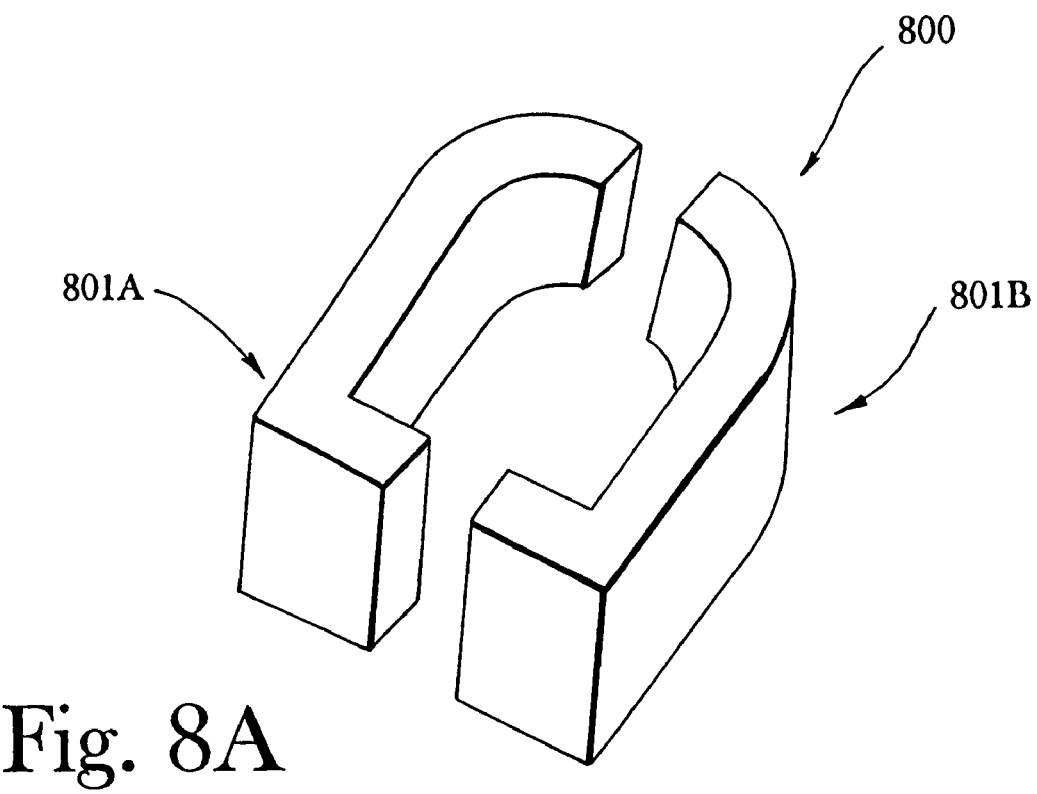
Fig. 8A
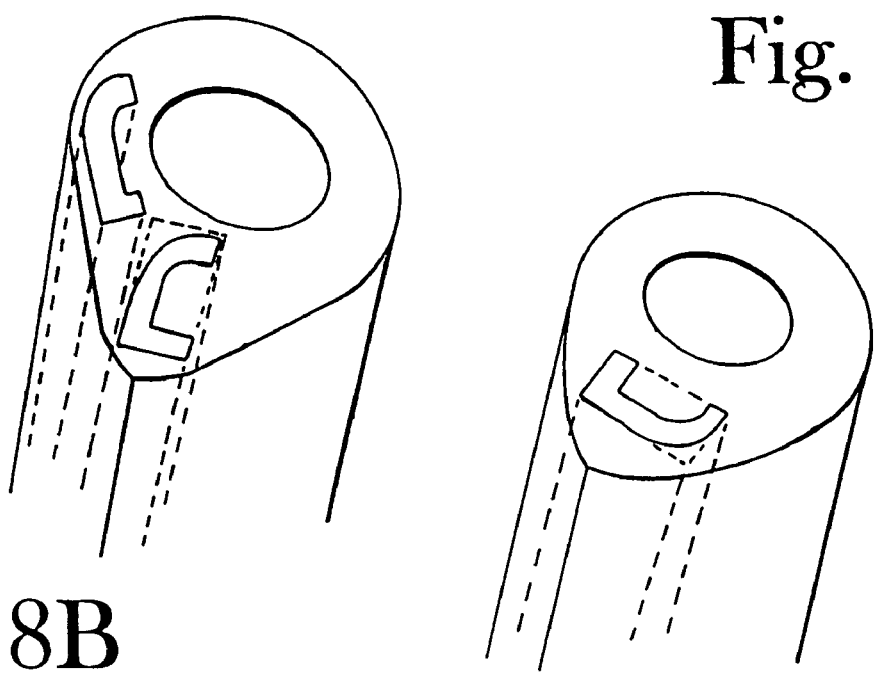
Fig. 8C
Fig. 8B

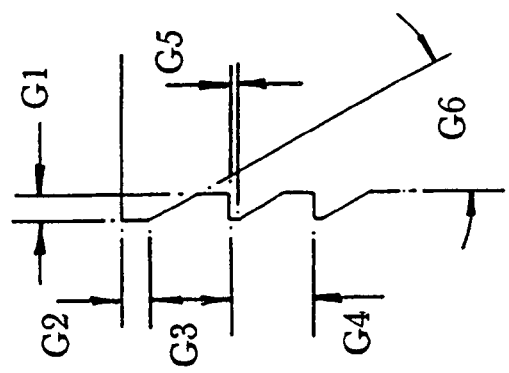
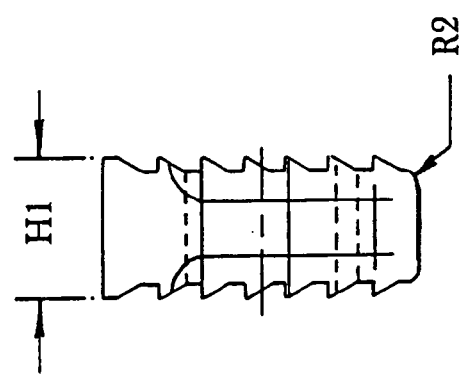
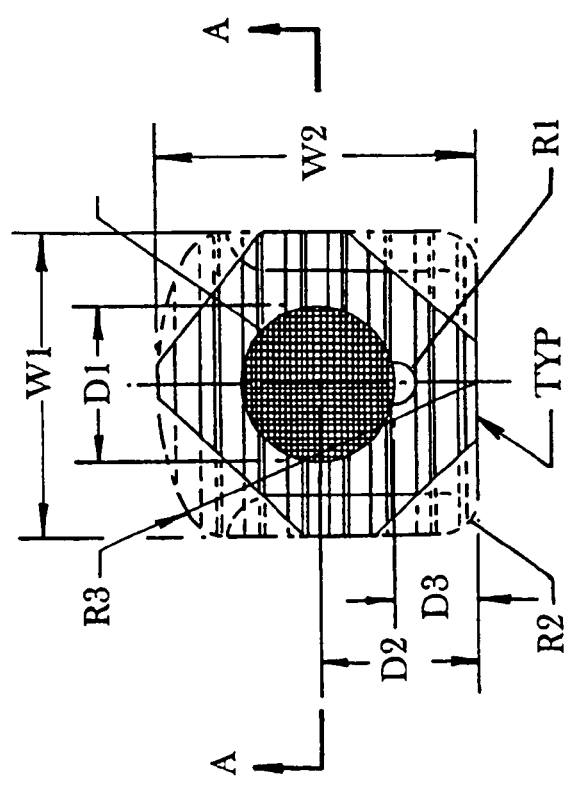
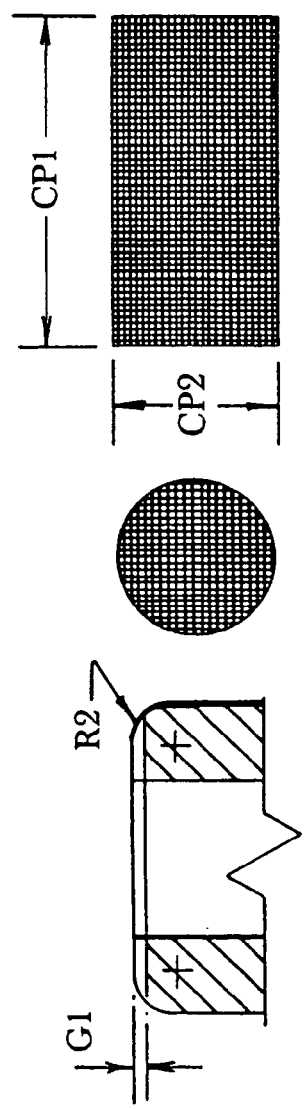

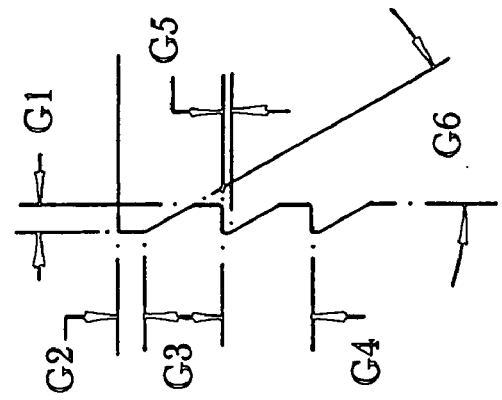
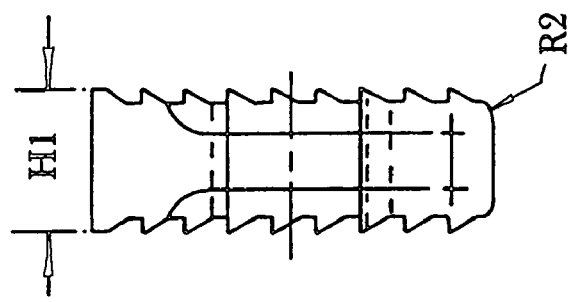
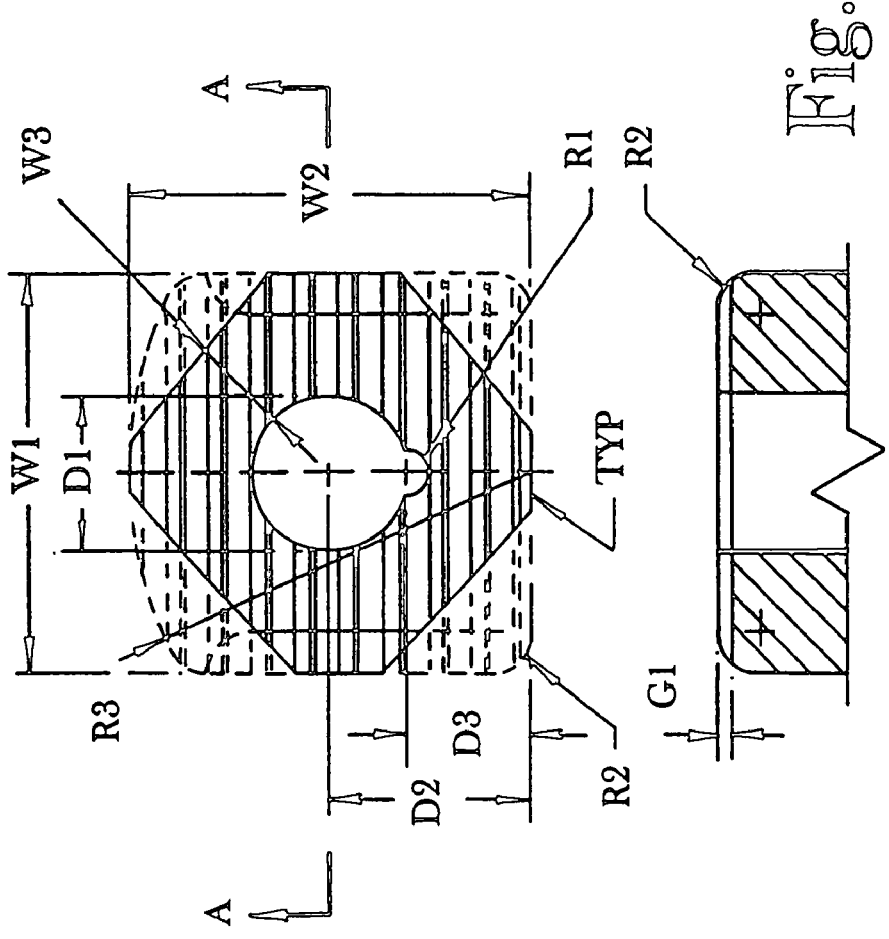
Fig. 16A  Fig. 16B  Fig. 16C  Fig. 16D

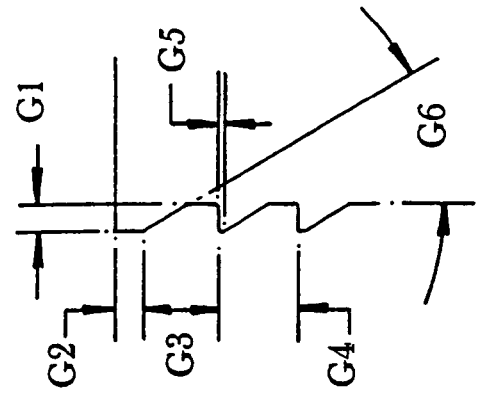
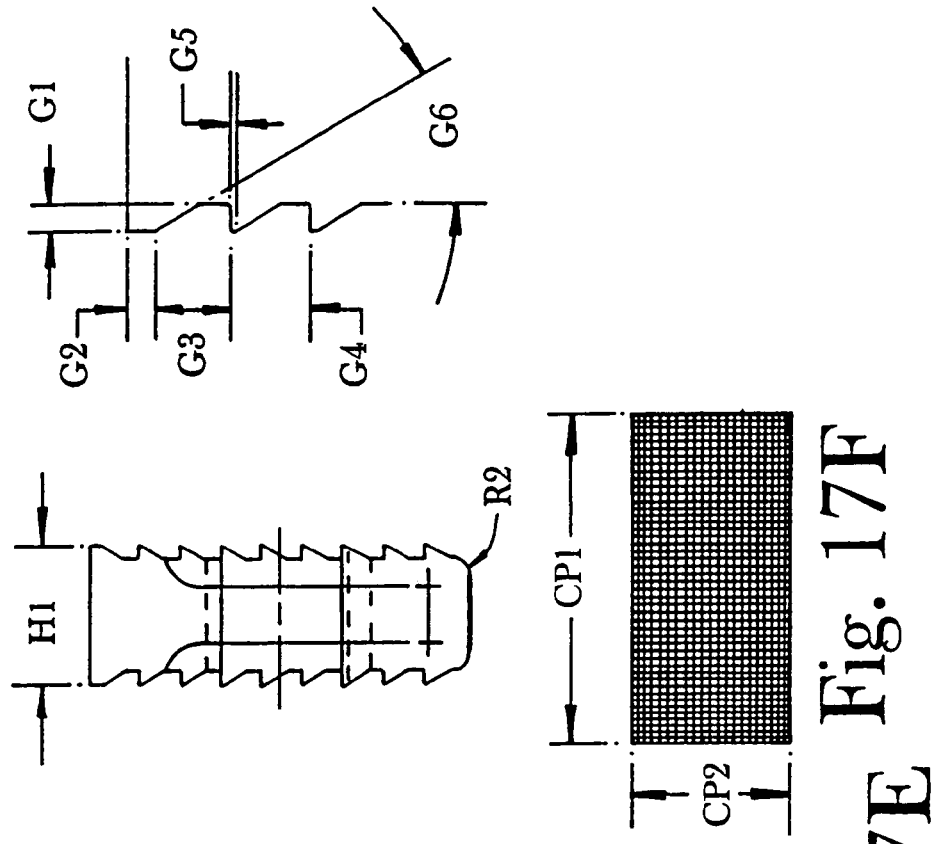
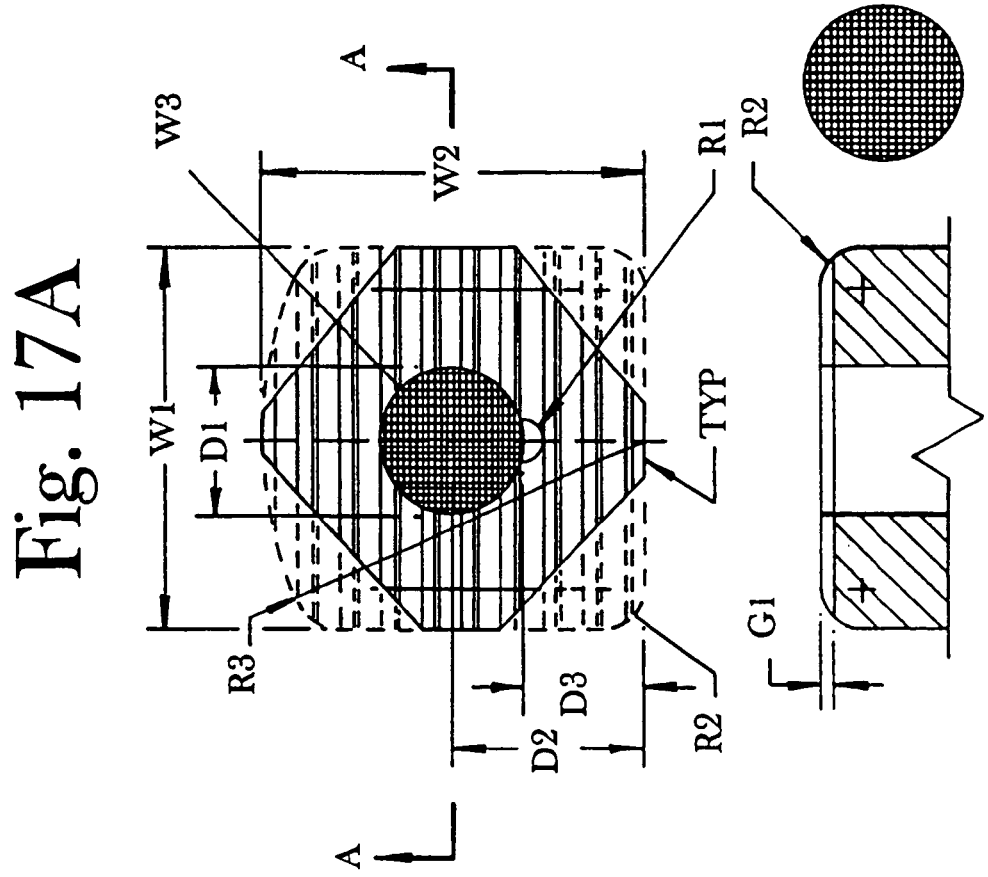
Fig. 17A  Fig. 17B  Fig. 17C
Fig. 17D  Fig. 17E  Fig. 17F

ELONGATED CORTICAL BONE IMPLANT

This application is a 371 of PCT/US98/17769, filed Aug. 27, 1998, which is a continuation-in-part of U.S. Ser. No. 08/920,630, filed Aug. 27, 1997, now abandoned.

1.0 BACKGROUND OF THE INVENTION

1.1 Field of the Invention

This invention relates to a cortical bone implant for use in cervical Smith-Robinson vertebral fusion procedures, as well as methods for the manufacture and use thereof.

1.2 Background Art:

Since at least the mid to late 1950's anterior cervical spinal fusions have been performed in order to alleviate chronic neck, arm and shoulder pain caused by trauma, disc herniation, or spondylosis (Robinson and Smith, 1955; Smith and Robinson, 1958). The classic procedure referred to as the Smith-Robinson cervical fusion employs a horseshoe-shaped graft to promote vertebral fusion (Robinson et al., 1962). The Cloward technique employs a cancellous bone dowel (Cloward, 1958), and the Bailey-Badgley procedure uses a strut (Bailey and Badgley, 1960). In a study comparing the compressive load capacity of the various implants used according to these procedures, it was found that the Smith-Robinson graft could sustain loads up to 344 N, the Cloward dowel could sustain loads of up to 188 N, and the Bailey-Badgley type could sustain loads up to 195 N, (White and Hirsch, 1972). In a modified Smith-Robinson procedure, the horseshoe-shaped implant is inserted with the cortical end of the implant located posteriorly, which has been reported to increase the fusion rate while decreasing the graft extrusion and collapse sometimes experienced with the Cloward dowels (Whitecloud and Dunsker, 1993). However, in a recent study evaluating the success and relief rates achieved according to these procedures, it was found that less than 100% success rate (fusion, patient improvement and absence of complications) was achieved, regardless of which method or implant was used (Grooms et al, 1996).

U.S. Pat. No. 5,306,309, discloses a spinal disk implant comprising a solid body of biocompatible synthetic material arranged to define a right-rectangular solid having two opposed side faces and two opposed transverse faces, including a convexly curved anterior face and a posterior face, for implantation in the intervertebral space. The discussion of vertebral and intervertebral morphology is hereby incorporated by reference.

U.S. Pat. No. 5,609,635, discloses a lordotic interbody spinal fusion implant comprising a wedge shaped metallic cage for insertion into the intervertebral space.

U.S. Pat. No. 5,306,307, discloses a ceramic spinal disk implant having a serrated edge.

None of these references disclose a cortical bone intervertebral implant having a substantially "D"- or bread-loaf-shaped structure having a canal into which osteogenic, osteoinductive, or osteoconductive materials may be packed, which sustains spinal loads, and which is remodeled into the spine in the course of fusion. Accordingly, the present invention addresses the need in the art for improvements to both the implant and the avoidance of post-surgical complications from anterior cervical fusions. The present invention provides a new cortical bone implant for use in achieving anterior cervical fusions when implanted according to the Smith-Robinson procedure. In addition, in view of the peculiar characteristics of bone, the present invention comprises unique methods and apparatuses for the manufacture of the substantially "D"-shaped cortical bone implant.

2.0 SUMMARY OF THE INVENTION

An implant composed substantially of cortical bone is provided for use in cervical Smith-Robinson vertebral fusion procedures. According to methods of this invention, the implant is derived from allograft or autograft cortical bone sources, is machined to form a substantially "D"- or other appropriately shaped implant having a canal into which osteogenic, osteoinductive, or osteoconductive material may be packed. The implant is inserted into the space between adjacent cervical vertebrae to provide support and induce fusion of the adjacent vertebrae.

3.0 BRIEF DESCRIPTION OF THE DRAWINGS

FIG. 1 provides several views of the fusion implant of this invention.

FIG. 2 provides views of the core cutter and drill assembly and the bone plug formed by cutting into the diaphysis of a long bone when such a core cutter and drill assembly is used.

FIG. 3 provides a view of broach as used according to this invention and an asymmetric-canal formed by use of such a broach.

FIG. 4 provides several views of an apparatus for machining a profile on the exterior surface of the implant of this invention.

FIG. 5 provides a view of an apparatus for inscribing retention teeth in the upper surface, lower surface or both upper and lower surfaces of the implant.

FIG. 6 provides several views and dimensions for specific embodiments of the implant of this invention.

FIG. 7 provides a view of a stacked embodiment of the implant of this invention.

FIG. 8 provides several views of an implant of this invention formed by juxtaposition of mirror image halves of the implant, as well as an embodiment useful for posterior lumbar intervertebral fusion procedures (PLIFs).

FIG. 9 provides a view of a stacked embodiment of the implant of this invention wherein the stacked constituents thereof are retained in registered relationship by press-fitting or otherwise bringing more than one implant into contact with each other and having a cancellous plug or other biocompatible material located in the central canal of each stacked implant, thereby acting as a retention pin.

FIGS. 12–17 show final profiles for implants produced according to the alternate method of FIGS. 10 and 11.

4.0 DETAILED DESCRIPTION OF THE INVENTION

Figure 1A:
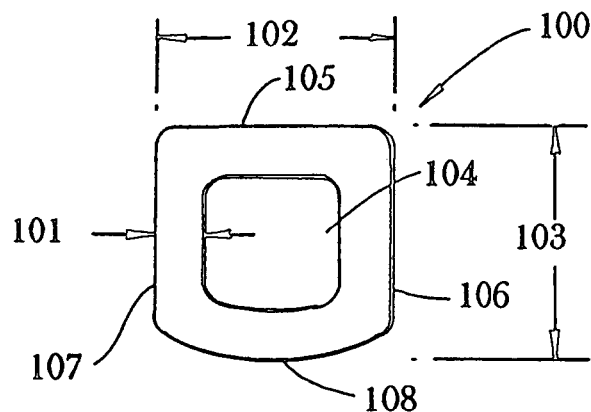

According to this invention, a substantially "D"-shaped cortical bone implant for cervical Smith-Robinson fusions is produced, preferably under aseptic conditions. Class 10 clean room processing is desirable, and sterilization of all machining tools is likewise preferred, (particularly after switching from one allograft donor to the next), so that the finished product may be treated by standard techniques known in the art (alcohol, peroxide, or like treatments), prior to storage and shipment to physicians for use in implantation procedures. Because of the peculiarities of working with bone, and in particular, because of the desirability of maintaining aseptic conditions while working with this material, novel approaches have been adopted in the production of the product of this invention.

The implant is preferably formed from cortical bone obtained from tibia, femur or other source of strong cortical bone. The bone source may be autograft or, due to possible complications at the donor site (infection, pain, delayed healing), is preferably, allograft bone. In addition, it is critical that the source bone be derived from a donor whose medical history is well known (absence of transmissible diseases, cancer, osteoporosis), and that the donor bone be obtained under aseptic conditions according to accepted practices in the art of tissue banking. In addition, extensive in vitro testing should be conducted to ensure the absence of pathogenic agents.

The approach adopted in describing the implant of this invention is to first provide a narrative disclosure of preferred methods for making the implant, followed by a detailed description of the implant itself, followed by a detailed description of various apparatuses and aspects of the machining process, and finally, a detailed description of the method of using the implant.

4.1 Narrative Description of Implant Manufacture

While any shape of cortical bone may be used to begin with, we have found that for consistent production of cortical bone which may be reliably machined, it is advantageous to commence with a plug of bone which extends from the exterior of the diaphysis of a long bone toward the intramedullary canal (where, in vivo, the bone marrow resides). The result is a bone plug or dowel which has an outer substantially cortical end and an internal end which is composed largely of soft cancellous bone. In cutting the bone plug, we have discovered that the use of a core cutter is convenient. This device comprises an outer coring element of any desired diameter, whereby the diameter of the bone plug is defined, and a centrally located solid drill bit, which provides a canal through the center of the bone plug as well as stability for the core cutting element. The core cutter-drill assembly is preferably torqued by an air drill, driven by sterile air, and the source bone is preferably immobilized in a sterilized vice during the core-cutting process.

We have discovered that in the above-described manner, cortical bone implants may be fashioned having heights, widths and lengths which are practically useful in the Smith-Robinson cervical fusion method. According to this method, the height of the implant is only limited by the distance from the exterior of the bone diaphysis to the intramedullary canal. However, we have discovered that, by this method, final implant heights from about 7 mm to about 14 mm may be produced, depending on the choice of bone source and the location on the bone from which the bone plug is cored. Since it is extremely rare for the cervical intervertebral space to extend beyond these limits, this method is therefore capable of supplying implants of required or useful heights. Likewise, the length and width of the implant are defined by the diameter of the core-cutter, and final lengths and widths of between about 7 and 14 mm are easily provided for by this method. In addition, where the need arises for heights between about 10 mm and 14 mm, or if difficulty is experienced in obtaining donor bone having a sufficient width from the exterior of the bone to the intramedullary canal to provide such heights, alternate methods of producing the implant of desired heights disclosed herein may be employed. For example, in a first such alternate method, implants of this invention are produced and then stacked to provide a unitary implant of the desired height dimensions. Such stacked implants may be maintained in a unitary association by drilling appropriate holes through the height of the implant, and inserting therein appropriate retention pins made from any desirable material, including cortical bone, bioabsorbable synthetic polymer, titanium or other metallic retention pins. Alternatively, the stacked implants may be retained in a unitary association by means of a plug of cancellous bone, hydroxyapatite or other biocompatible, osteoconductive or osteoinductive material, and press-fitting the stacked implants to achieve the desired height (see FIG. 9). In a further alternate method, a section of cortical bone along the long axis of a long bone may be machined according to methods known in the art. By then further shaping and cutting appropriate heights in such cortical bone, and bringing halves of the implant into juxtaposition with each other, implants of any desired shape and height are produced. In yet a further alternate procedure, (see FIGS. 10–17), unitary implants of this invention of essentially unlimited height are produced by length-wise sectioning the anterior margin of the tibia or linea aspera of the femur, segmenting the substantially triangular cortical bone to desired heights, drilling a cannulation through the segments thus produced, and finally shaping the implants to desired dimensions, as defined below for the first principal method of making the implant of this invention.

Continuing with a description of the first method for making the implant of this invention, the cancellous bone on the internal side of the bone plug is removed by any convenient means, including with a saw, an abrasive means such as a diamond tipped rotary sander, or a tooling bit mounted in a lathe, to produce a "washer" shaped piece of substantially cortical bone. Both the internal and external ends of the bone plug should be machined flat, thereby forming a top face and a bottom face, each of which is substantially planar, and preferably parallel. While the cancellous bone is partially or completely removed by this process, there remains a slight difference in the density of the bone from the external (cortical) to the internal (cancellous or originally intra-medullary) aspect of the bone plug. It is desirable to record the orientation of the bone plug as subsequent machining steps proceed most efficiently when machined from the external aspect toward the internal aspect.

In order to accommodate subsequent machining steps and to provide an orientation to the implant according to which the surgeon may properly insert the implant, the circular internal canal formed by the centrally located solid drill bit of the core-cutter is modified to form an asymmetric shape, such as a key way. This may be achieved by any of a number of different means, including drilling a slot into an aspect of the internal canal closest to the external (more dense cortical) end of the dowel. In one embodiment of this invention, we have found that an implant of consistently good final quality may be machined by conversion of the circular canal into a substantially "D" shaped canal having three essentially rectangular walls and a fourth convexly curved wall. We have found that it is desirable for the curvature of the convexly curved wall to approximate the external curvature of the bone plug. This modification may be achieved by any of a variety of means. However, we have invented an efficient means by which consistently usable implants may be reproducibly machined. This is accomplished by immobilizing the implant, for example in an arbor press assembly, and, preferably from the originally cortical external (denser) end of the implant, slowly forcing a broach through the originally circular canal. The broach is preferably a hard metallic member having a plurality of spaced-apart ribs or rings machined therein, with indentations provided between each ring which thereby form the spacing between adjacent rings. In addition, the edges of each ring are desirably very precise, angular, and sharp, such that as the broach is forced through the originally circular internal canal, the sharp cutting edge of each ring shaves off an incremental amount of bone as the ring passes through the implant. Each ring of the plurality of rings has a shape which, starting at the insertion end of the broach is tapered from an essentially circular shape to any desired final shape for the canal. Accordingly, in one embodiment of this invention, the rings transition from a circular shape to a substantially "D"-shaped profile or any other desired shape over several inches and over a plurality of spaced apart rings. It will be appreciated that the length of the broach and the number of rings used is defined by the amount of bone that must be removed to form the new shape, the width of each ring and the width of the space between each ring. Removal of no more than about 0.004" of bone by each ring has been found to be a sufficiently small transition to ensure that the vast majority of implant blanks survive this machining step. Broaches of approximately 6" in length have been found adequate for most implant shapes, but for very asymmetric shapes (e.g. an implant which is 11 mm wide and 14 mm long), more bone would need to be removed to form the "D"-shaped canal than from a symmetric implant (e.g. a 14 mm wide by 14 mm long implant). This need may be accommodated by use of more than one broach, with the shape of the insertion end of each consecutive broach substantially matching the shape of the last ring on the previous broach.

Having formed an asymmetric shape, such as a key way, from the internal canal running through the implant, we have found it desirable to modify the external profile of the implant from a substantially circular shape to another desired form. In one embodiment of this invention, the external form of the implant is machined so as to proportionately match the shape of the substantially "D"-shaped internal canal. An external "D"-shaped profile has been used in implants known in the art (see for example U.S. Pat. Nos. 5,306,309; 5,522,899) made from materials other than bone, because of the ability of the convexly curved face of the implant to substantially match the curvature of the anterior aspect of the intervertebral disk into which the implant is to be inserted, as well as to provide efficient spinal load distribution over the remainder of the implant. However, due to the peculiar nature of bone, and the requirements of aseptic or sterile manufacturing, inventive methods and apparatuses were required to produce the desired external profile for the cortical bone implant. It will be recognized that, based on the instant disclosure, a substantially "D"-shaped external profile of the implant may be machined by a variety of means which vary from the precise methods disclosed herein. In addition, other external profiles than the "D"-shaped profile are likewise enabled by modifications of the methods and apparatuses disclosed herein for formation of the "D"-shaped external or internal profile. Thus, according to one alternate method of making the implant of this invention, for example where the linea aspera of the femur is sectioned or where the anterior margin of the tibia is sectioned, an external profile that substantially varies from a "D"-shaped device may be produced, (see FIGS. 10–17).

We have found it convenient and reproducible to use either of two principal methods for machining the external profile. The implant, with the "D" or alternately shaped internal canal being used as a key way, is fitted onto the end of a spindle which precisely matches the shape of the internal canal of the implant, thereby providing purchase for machining of the external profile of the implant. In a first preferred method, as the implant is rotated on the spindle, it is contacted with an asymmetric generator (grinding) wheel attached to a cog which meshes at a known registration point with a cog to which the spindle with the implant is attached. The speed of rotation of the exterior of the spindle mounted implant, and the exterior of the generator wheels are designed to differ such that as the generator wheel and implant are contacted and are rotated in fixed registration, the generator surface (which is preferably an abrasive diamond plated surface), grinds bone from the external surface of the implant, to form a profile thereon defined by the asymmetric shape of the grinder wheel.

In a second external profile generation method, the implant, with the "D" or alternately shaped internal canal being used as a key way, is fitted onto the end of a spindle which precisely matches the shape of the internal canal of the implant, thereby providing purchase for machining of the external profile of the implant. In this method, the spindle is affixed to an asymmetric cam which rotates concentrically with the spindle, and therefore the implant. The thus mounted implant is contacted with a cutter means, such as a sharp bit having cutting edges which rotate about an adjacent axis. The implant mounted spindle riding on the asymmetric cam is biased to contact the rotating cutter, which thus traces a profile onto the exterior of the implant defined by the shape of the asymmetric cam. For purposes of this disclosure, use of the term "asymmetric cam" should be understood to mean any desirable shape such that upon production of the implant, the shape thereof is defined by that of the asymmetric cam. Shapes contemplated by this disclosure include, but are not limited to, elliptical shapes, D-shapes, partially curved shapes, and the like. The implants produced according to any of the alternate procedures are likewise shaped, although the final shape may vary depending on the size of the bone stock used (see for example the final shapes of the device shown in FIGS. 12–17).

Once the external profile has been machined, the implant is removed from the spindle, and the machining of the implant may either be terminated, to provide a substantially "D"-shaped cortical bone implant with flat upper and lower surfaces, or an external feature may be machined into the upper and lower surfaces to prevent backing out of the implant upon insertion into the intervertebral space. This may be achieved by a number of means, such as by machining annular rings, indentations and projections, ribbing or teeth into the upper, lower, or both surfaces of the implant. In a preferred embodiment of this invention, the implant is passed through a set of opposing jaws bearing teeth which broach a tooth-shaped profile into the implant as it is forced through the jaws. Alternatively, the implant is passed several times over a ridged surface which cuts the desired tooth profile into the upper, lower or both surfaces of the implant. Preferably, the thus formed teeth angle toward the anterior (convexly curved) face of the implant to prevent backing out of the implant once it is inserted into an appropriately shaped cavity formed in the intervertebral space in an anterior aspect of the cervical spine. In order to accommodate the difficulty surgeons experience in forming precise angles when forming such cavities in the spine, (see for example U.S. Pat. No. 5,397,364 disclosing a beveled edge to reduce trauma upon insertion of a metallic spinal implant), a beveled edge of defined radius is preferably machined into three faces of the implant, but leaving the anterior face unbeveled. The sharp anterior edge, like the teeth in the upper and lower surfaces of the implant, retards backing out of the implant.

4.2 Detailed Description of the Implant

Figure 1B:
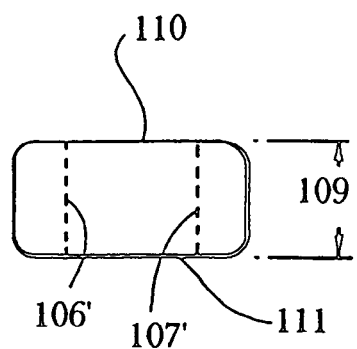
Figure 1C:
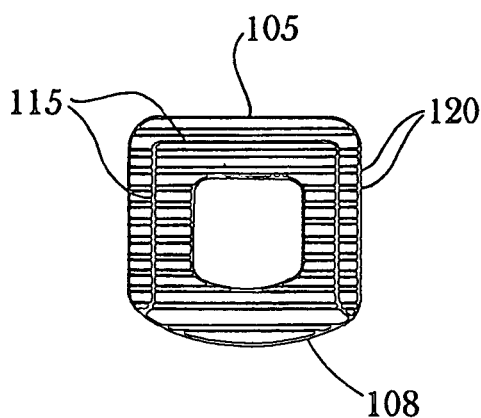
Figure 1D:
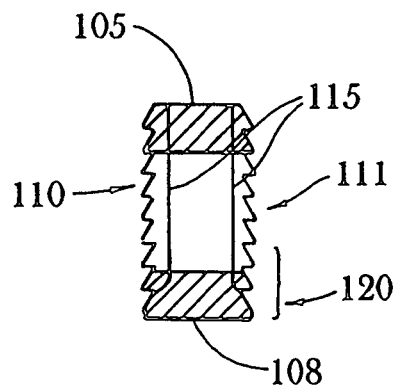
Figure 1E:
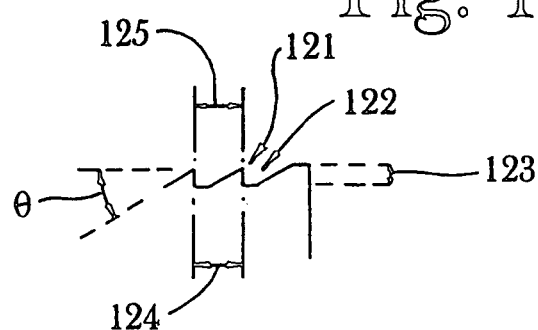

Referring now to FIG. 1A, there is shown a top view, as if viewed from the top of the spinal column, of a substantially "D"-shaped cortical bone implant 100. The implant has a wall thickness 101, a length 103, a width 102, and an internal canal 104, which fall within desired tolerances (see discussion below). The implant comprises four contiguous walls, including a substantially straight rear wall 105, substantially straight side walls 106 and 107, and a preferably curved front wall 108. In FIG. 1B, there is shown a side view of the implant 100, revealing the height 109, of the implant. In addition, this view shows, in outline, the internal side walls 106' and 107' of the internal canal, 104. It also shows the top 110 and bottom 111 surfaces of the implant. In FIG. 1C, there is shown a top view of an embodiment of the implant 100 in which an external feature 120 has been inscribed onto the top 1110 and bottom 111 surfaces of the implant. In addition, a "radius" or bevel 115 is shown on the two side and posterior edges of the implant. FIG. 1D shows a side view of the implant 100 in which the inscribed feature 120 can clearly be seen in the top 110 and bottom 111 surfaces of the implant. In this view, it can be seen that the external feature 120 has the side profile of a set of teeth, all of which angle toward the anterior face 108 of the implant. An outline of the bevel 115 is also evident in this view, as is the rounded posterior edge 105. As can be seen, in this embodiment of the invention, the anterior edge 108 is maintained with a sharp edged. In FIG. 1E, there is shown a detail of one embodiment of the inscribed feature 120 on the portion of the implant indicated in FIG. 1D. In a preferred embodiment, the feature 120 defines a tooth-like structure, with teeth 121 separated from each other by concavities 122. An angle θ defines the grade of the concavity as it ramps to the tooth. The tooth height 123, space between teeth 124, and aperture of the concavity 125 may all be defined by the manufacturer to optimize retention of the implant within the cervical spine after proper placement.

4.3 Detailed Description of the Method of Manufacturing the Implant

Because of the peculiar nature of bone, and the desirability of sterile or aseptic manufacturing, specific and specialized procedures and apparatuses are required for successful formation of the implants of this invention. Those skilled in the art will recognize that, based on the methods and apparatuses disclosed herein, the implant of this invention may be manufactured by alternate means suggested by those described herein. Nonetheless, through careful design and knowledge of bone structure, instruments for the manufacture of the implant of this invention have been invented for this purpose. In what follows, specific details with respect to preferred method and apparatuses for making the implant of this invention are provided. It should be recognized that the invention should not be construed as being limited to these specifics.

Figure 2A:
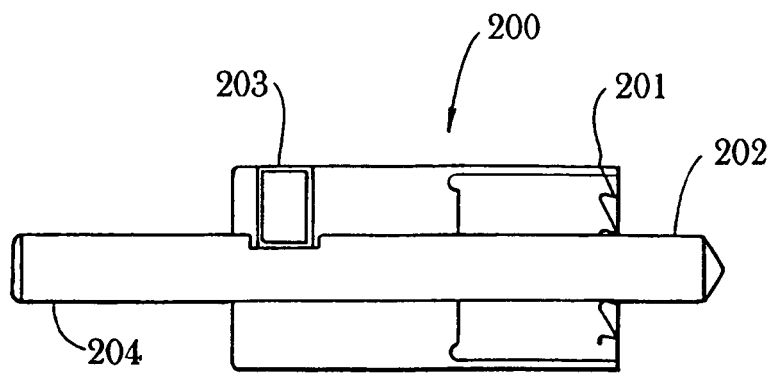
Figure 2B:
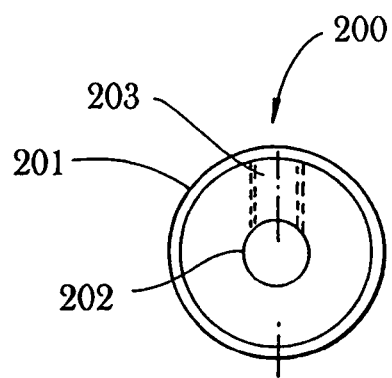
Figure 2C:
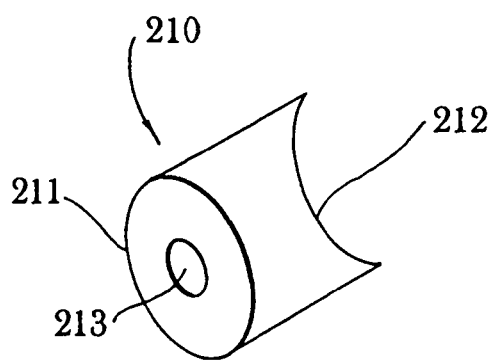
Figure 2D:
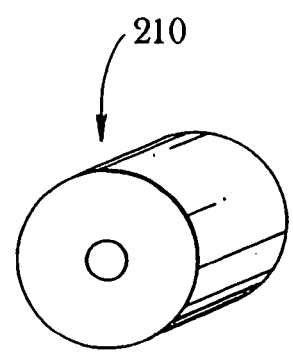

Referring to FIG. 2, there is shown in side view in FIG. 2A a core cutter 200, having a core bit 201 which is affixed by a set screw 203 to the shaft 204 of a drill bit 202, centrally located within and coaxial with the core cutter. In FIG. 2B, an end-on view of the core cutter 200 is provided showing the set screw 203 in outline. FIG. 2C shows a side view of the bone plug 210 which is formed by cutting a plug of bone from the diaphysis of a long bone using the core cutter 200. At one end, 211, originally the external cortical surface of the bone shaft, there is a substantially cortical bone surface through which a hole 213 is formed by the central bit 202 of the core cutter 200. The other end, 212, is an irregular and bone surface which, in vivo, formed part of the wall of the intramedullary canal. Cancellous bone or other microstructure at the end 212 is removed, and both ends are ground, cut or otherwise machined to be substantially flat and parallel, to form the substantially cortical bone plug 210 shown in FIG. 2D.

Referring to FIG. 3, there is shown in FIG. 3A an internal canal profile broaching tool 300. A plurality of spaced-apart ribs or rings 301 are provided along the length of the broach which taper from a substantially circular shape at the insertion end 302 of the broach, to substantially "D"-shaped rings 303 (or any other desired shape) at the completion end 304 of the broach 300 (intermediate ribs 305 are not shown; rather, the outline of the taper angle is shown).

A notch or groove 306 is provided in the broach completion end 304 for releasably affixing the broach into a means, such as a press, for forcing the broach through the implant canal. In FIG. 3B, there is provided an end-on view of the cancellous bone plug 310 after the broaching procedure is completed. As can be seen, the internal canal 104 has been converted from a circular canal into a substantially "D"-shaped canal. As will be appreciated from this disclosure, any of a number of different asymmetric shapes in the internal canal 104 may be defined by this or analogous means, the principal goal being to provide a purchase (referred to herein as a "key way") within the implant for external machining of the implant. In one embodiment (see FIG. 9), the canal may be retained as a substantially circular canal, and a slot 904 is machined therein to provide the necessary asymmetry to form a key way.

Figure 4A:
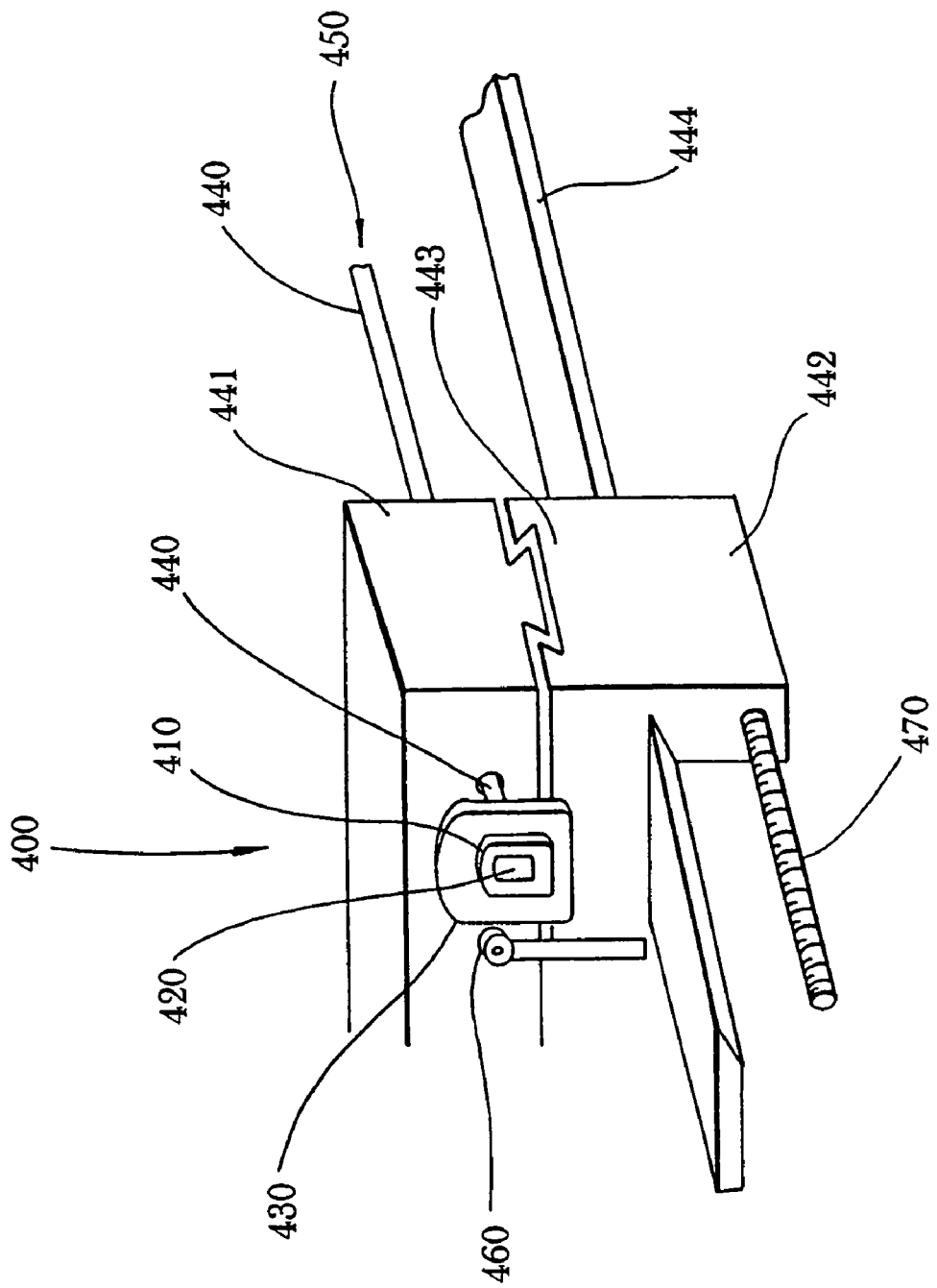

Having formed a key way within the implant, it is possible to modify the external profile of the implant. In one aspect of this invention, referring to FIG. 4A, this is conveniently achieved by affixing the implant 410 to the spindle 420 of a lathe 400. The spindle shaft 440 extends, through bearings (not shown), to a means 450 (such as a handle or a motor) for rotating the spindle. Affixed to the spindle-shaft is a cam 430, the shape of which defines the ultimate external profile of the implant 410. The spindle shaft 440 and bearings are mounted in a cross slide 441, which translates in a first plane, referred to as the "Y-plane". Motion in the Y-plane is limited by contact of the cam 430 with a limiting means 460 such as a cam follower, which remains in register with a carriage 442 which translates along a plane, the "X-plane", transverse to the Y-plane motion of the cross-slide. The cross-slide is mounted in a slide-way 443 of the carriage 442, which in turn is slideably mounted on the bed 444 of the lathe, such that the carriage 442 is permitted to translate along the X-plane. Travel of the slide 442 along the X-plane is limited by means of a stop screw 470.

Further detail of this means for generating the external profile of the implant is provided in FIG. 4B, which provides a side view of one specific embodiment of the implant external profile generator 400. An air driven turbine within housing 401 provides a source of torque to turn a shaft 402. A means for cutting or grinding the external surface of the implant 410, such as an appropriately fashioned cutter or bit having a non-cutting end 403 for fixation to the shaft 402.

Extending from the non-cutting end 403 which has a first diameter, is a cutting surface 404, having a second, smaller diameter. A "shoulder" 405, forms a radius extending between the smaller diameter of the cutting surface 404 and the larger diameter of non-cutting surface 403.

The cutting surface 404 is contacted with the implant blank 410, mounted on spindle 420, to which, as described above is mounted an asymmetric cam 430. The thus mounted implant blank 410 is brought into contact with the cutting surface 404, by virtue of translation in the X-plane of the carriage 442. The spindle 420, and thus the asymmetric cam 430 are rotated, manually or by motor driven means, through shaft 440 and handle 450 which are attached concentrically with the cam 430. Preferably, the asymmetric cam 430 is elastically biased toward a stationary cam follower 460. In this fashion, after several revolutions of the handle 450, the shape of the asymmetric cam 430 generates the desired external profile of the implant 410 riding on the spindle 420, through contact with the rotating cutting surface 404.

To ensure that the implant blank is machined only up to the point that the forward edge 4111 of the implant approaches but does not contact the "shoulder" 405 on the cutter, a stop screw 470 is provided. The stop screw 470 is set to prevent further advancement of the implant blank 410 by stopping advancement of the carriage 442 when the leading edge 471 of the stop screw comes into contact with a measuring screw 480. The appropriate setting of the stop screw 470 is achieved at the start of the milling process by first placing the implant 410 between the end 481 of the measuring screw 480 and an anvil 482, and tightening the measuring screw 480 until it just makes contact with the implant. In this fashion, the measuring screw 480 and anvil 482 essentially form a micrometer, with the gap being defined by the width of the implant. Both the measuring screw 480 and anvil 482 are housed within a measuring slide 483 which, when slid all the way to the left as shown in FIG. 4B, abuts a rotateable stop cam 490, retained within the same slide-way as the measuring slide 483 by a retainer 484. The rotateable stop cam 490 may be set in either of two positions, which produces a difference in the stopping point of the stop screw 470 of approximately 0.06". The significance of this difference is that the first position arrests advancement of the stop screw 470 (and therefore the carriage 442) just before the implant 410 contacts the radius shoulder 405 of the cutting surface 404. In the second position, the stop cam 490 allows the stop screw to advance the additional approximately 0.06" to allow contact of the implant 410 with the shoulder 405 of the cutting surface 404 to thereby bevel the edges of the implant 410 that are thus contacted. Accordingly, in the pre-milling setup, the stop cam 490 should be rotated such that the stop screw 470 is forced to stop the extra 0.06", following which a further processing step may be carried out in which the stop cam 490 is rotated to the second position in which the stop screw 470 is allowed to advance this additional approximately 0.06".

In FIG. 4C, there is provided an end-on, rear view (i.e. looking from the handle 450 toward the spindle 420) of the asymmetric cam 430, the spindle 420 and the implant 410. In addition, in this detail view, an additional feature in the asymmetric cam 430 is seen as a diminution in the thickness along three faces 431 of the asymmetric cam 430 which is a relief in the rear of the asymmetric cam 430. The significance of this relief 431 is that it restricts the contact of the implant 410 with the shoulder 405 to the extent defined by the relief in the rear of the asymmetric cam 430. As noted above, in fashioning an implant site in the intervertebral space during a partial discectomy, surgeons are unable to produce perfectly sharp angles. To accommodate this imperfection, to prevent trauma upon insertion of an implant with sharp edges, and to create as tight-fitting an implant as possible, the fashioning of a bevel around the edges of the implant that are inserted into the intervertebral space created by the surgeon is desired. At the same time, in order to prevent backing out of the implant, it may be desirable to retain a sharp anterior implant edge, and therefore the relief in the cam 430 does not extend completely around the cam. Thus, upon completion of the external profile of the implant 410 as described above, the carriage 442 is backed away from the cutter, the stop cam 490 is flipped to its second position allowing advancement of the stop screw 470 the additional approximately 0.06" mentioned above. At the same time, a shot pin 432 is advanced into the relief 431 by means of a shot pin mover 433, thereby allowing rotation of the cam 430 only to the extent permitted by the shot pin 432 as it rides within the relief 431. With the shot pin 432 riding in the relief 431, the "shoulder" 405 contacts the leading edge 411 of the implant blank 410, thereby rounding three edges of the implant 410. After machining the leading edge 411 of the implant 410, the implant is removed from the spindle 420, turned around, and re-positioned on the spindle 420, to inscribe the bevel on three edges of the other side of the implant.

In FIG. 4D, a frontal view is provided of the spindle 420, the implant 410, the asymmetric cam 430, and the cam follower 460. Also shown is the cam adapter 461, by means of which the cam follower 460 is affixed to the carriage 442, and by means of which the cam follower 460 maintains the cutting surfaces 404/405 in contact with the implant 410 as defined by the shape of the asymmetric cam 430. Also shown is a part of the cross-slide 441, which is preferably biased or which may be pushed manually toward the cam follower 460.

In FIG. 4E, a side detail view is provided of the stop cam 490. In this view, a stop cam handle 491 is shown which allows the operator of the implant outside profile generator to fix the stop cam 490 in a first position A, and a second position B, whereby additional travel of the stop screw 470, and thereby advancement of the carriage 442, is provided in position 1B, of about 0.06" due to the difference in the distances shown for these positions.

By means of the apparatuses and method described above, a cortical bone implant 100 as shown in FIG. 1 having a substantially "D"-shaped external profile, and a substantially "D"-shaped internal canal is produced. Naturally, based on this disclosure, those skilled in the art will appreciate that other shapes, both for the external profile and internal canal of the implant may be produced. For example, an ellipsoid is produced by the above described methods simply by modification of the shape of the asymmetrically shaped cam 430, and the internal canal shape may be modified by drilling, routing, or broaching using a broach that tapers to any desired shape. The thus formed implant may be used after machining as described, followed by appropriate cleaning methods known in the art (e.g. bathing in alcohol, peroxide treatment etc.). In addition, however, it may be desirable to inscribe an external feature on the upper surface 110, the lower surface 111, or both. Such a feature may take any desirable form, such as annular rings, indentations, projections, ribbing or teeth. In a preferred embodiment, teeth sloping toward the anterior aspect 108 of the implant are inscribed onto the top 110 and bottom 111 surfaces of the implant by forcing the implant through opposed broaches bearing inscribing teeth. Alternatively, the upper 110, lower 1111 or both surfaces in turn may be repeatedly run, manually or by a machine-driven means, over an appropriately fashioned jaw bearing abrasive teeth such that the required profile of teeth are inscribed into the surfaces of the implant. Desirably, the successive teeth of the jaw are incrementally raised in height such that each tooth is only required to remove a small amount of bone (about 0.004" per tooth, to a total depth of 0.015"). In addition, it is preferred that the rake (angle of the teeth) be sufficiently sharp as to allow the implant to bite into the implantation site, without at the same time being so sharp as to be excessively brittle.

Figure 5A:
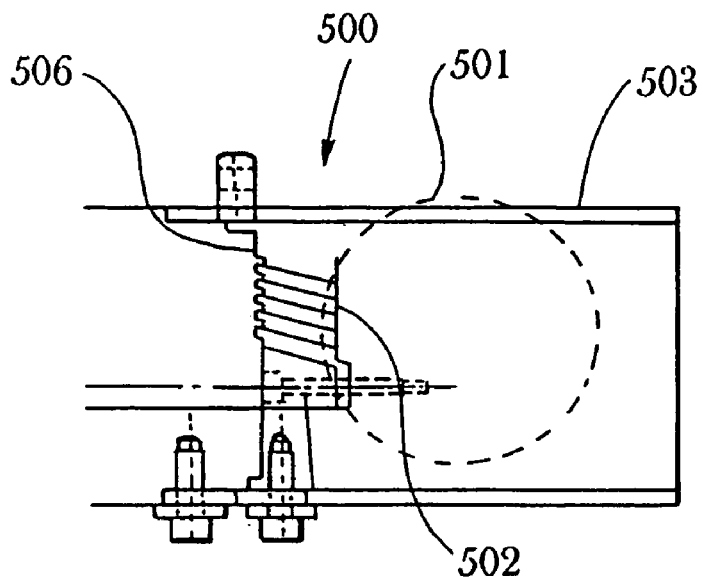
Figure 5B:
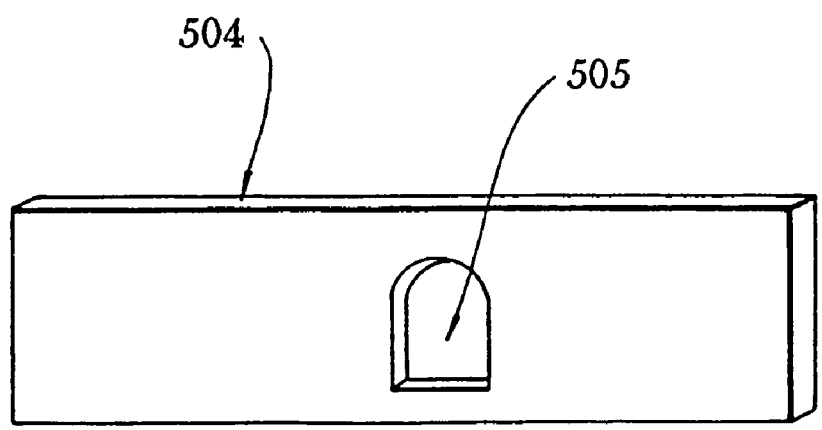

In FIG. 5, FIG. 5A, there is provided a top view of one side of one embodiment of blades 502 for use in a broach assembly 500 for inscribing teeth into the top 110, bottom 111 or both surfaces of the implant. In outline, there is shown a lock-down handle 501 for clamping the assembly of blades 502 to a base 503. By bringing a mirror image jaw into register with the depicted broach, a space is formed between the opposing teeth 502 at a distance sufficient to accommodate passage of the implant therebetween, provided that the teeth abrade recesses into the top and bottom surfaces of the implant 100. To ensure proper engagement of the blades 502 and the implant 100, there is provided a non-cutting surface 506 for contacting the implant 100 as it is introduced into the broach assembly 500. The non-cutting surface 506 acts as a type of micrometer, forcing the cutting surfaces of the teeth 502 sufficiently apart to properly engage the implant as it passes through the broach assembly 500. In FIG. 5B, there is provided a side view of an implant mounting device 504 having a "D"-shaped cavity 505 into which a "D"-shaped implant may be fitted for passage through the opposing jaws of the broaching jaw apparatus 500. The resultant implant has the profile shown in FIGS. 1C–1E.

Figure 5C:
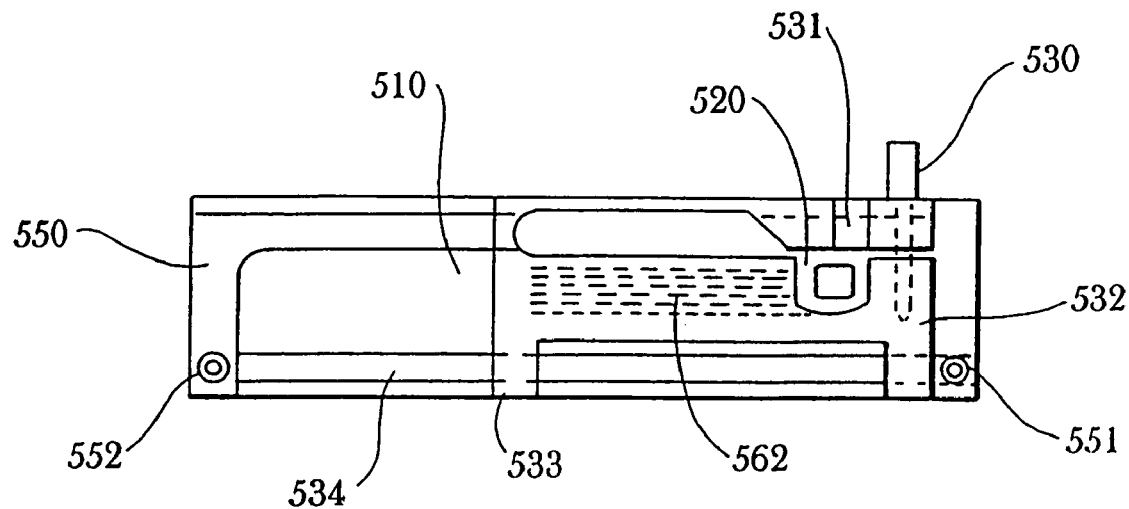
Figure 5D:
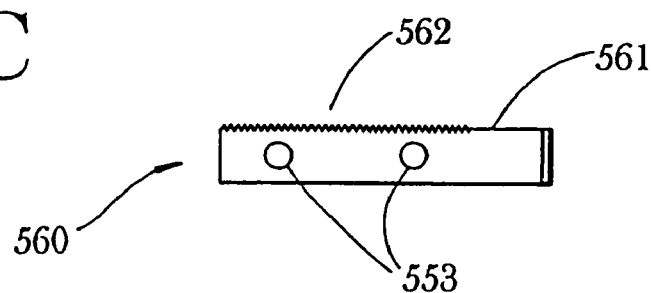
Figure 5E:
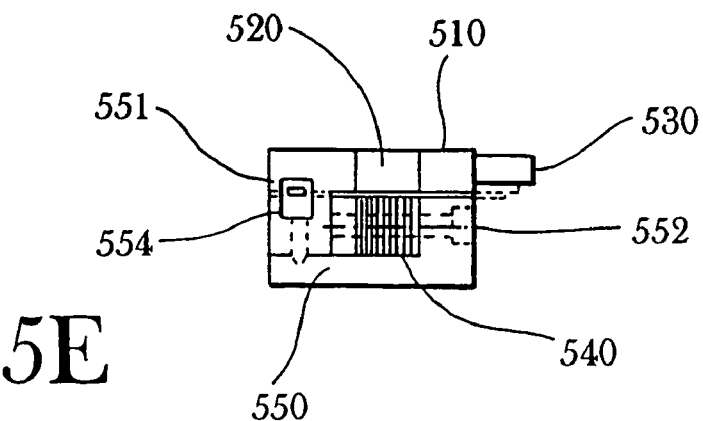

In FIGS. 5C–5E, there is shown an alternate apparatus and method for fashioning the retention teeth in the implant. In FIG. 5C, there is shown a carriage 510 having an appropriately dimensioned slot 520 for receiving the implant to be grooved. A tensioning screw 530 brings a retention arm 531 into juxtaposition with carriage housing member 532, thereby clamping the implant into position within slot 520. Through carriage housing members 532 and 533, there is aligned a guide-rod 534 for guiding the carriage containing the implant as it is raked across a blade assembly 540, over which said carriage 510 is made to pass. Said guide rod 540 also conveniently acts as a hinge, allowing the carriage 510 to swing upward for implant loading and also permitting the carriage to move down toward the base as the implant surface is cut on each successive pass of the carriage over said blade assembly 540. The blade assembly 540 is bolted within a base 550 over which said carriage 510 slides. Said base 550 also acts to receive fixation screws 551 and 552 which retain said guide rod 534 in place. A plurality of individual blades 560 are placed in a recess 554 in the base 550 and are maintained in registered position by retention screws 552 passing through retention holes 553 in each blade. Each blade 560 has an initial non-cutting surface 561, which is approximately 0.015" below the cutting surface 562, which in combination with said plurality of blades, forms a flat loading area for implant insertion into said slot 520. FIG. 5D provides a side view of one blade 560, while FIG. 5E provides an end on view of the carriage 510 as it sits above the base 550. Accordingly, the implant is inserted into the slot 520 with the carriage 510 swung up from the base 550. The carriage is then swung down into the starting position with the implant making contact with the non-cutting surfaces 561 of the plurality of blades. The implant is depressed so that it is forced snugly against the non-cutting surface, and then tensioned into place with the retention screw 530. Thereafter, the carriage is slid several times over the base 550 such that the cutting surfaces 562 of the plurality of blades thereby inscribe the desired tooth structure into the top surface, the bottom surfaces or both (after switching the implant around) surfaces of the implant. When the metallic bottom of the carriage comes into contact with the base, the machining of the implant is complete.

Figure 6F:
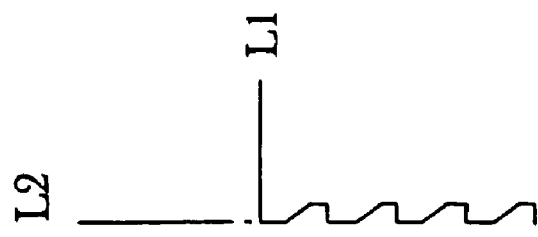
Figure 6E:
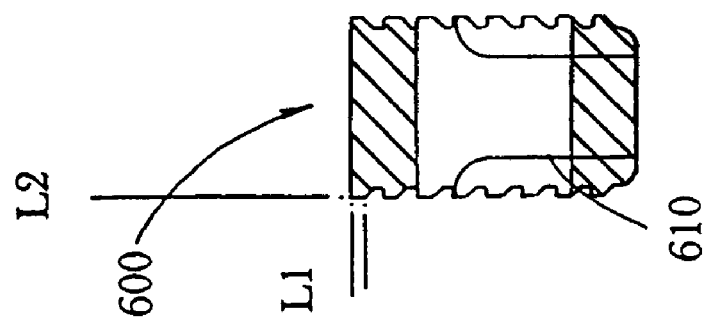
Figure 6D:
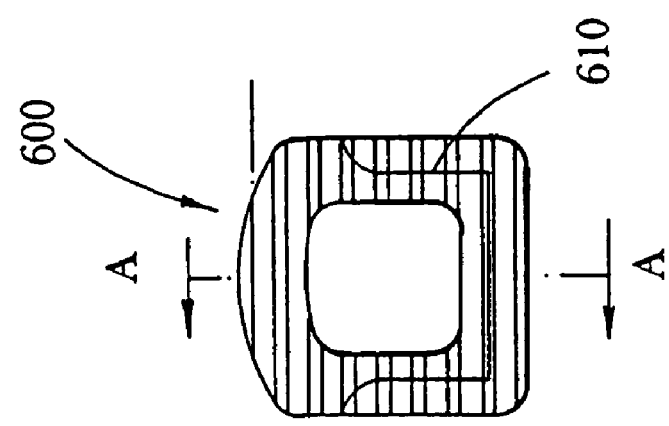
Figure 6G:
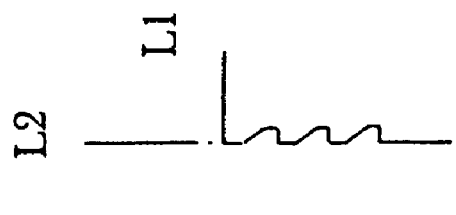
Figure 6H:
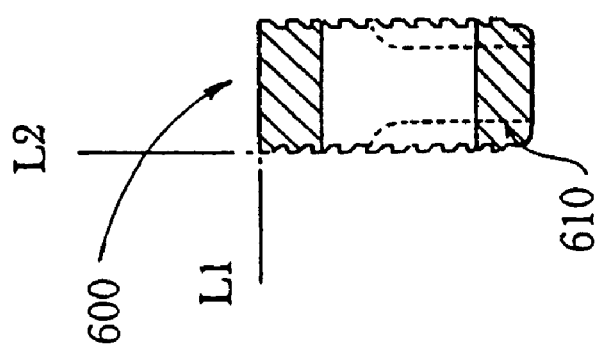
Figure 6I:
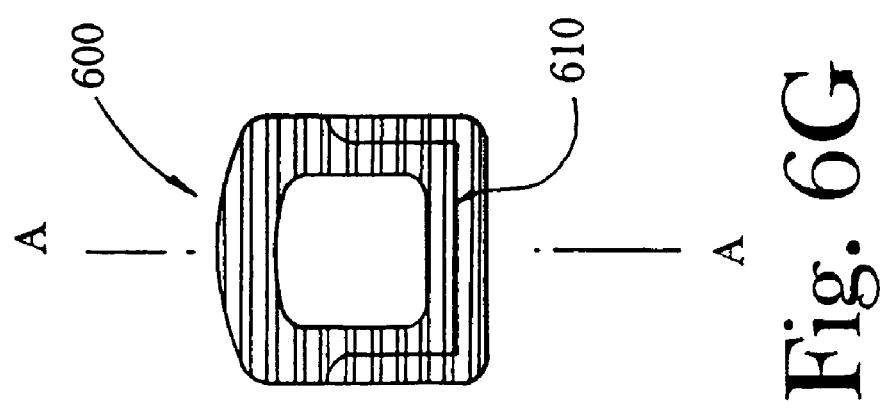

In FIGS. 6A–I, there is provided a view of three different cortical bone implants according to this invention having particular geometries by way of example and not limitation. In FIG. 6A, there is shown an example of an implant 600 which has a height of 7 mm, a width of 11 mm, and a length of 14 mm. In addition, dimensions of various radii of the implant are provided. Note the effect of the "shoulder" 405 of the cutter which produces the a 0.059" radius and indent profile 610 starting at the approximate center of the part and proceeding around to the opposite side of the implant, i.e. around three faces of the implant. In FIG. 6B, the implant 600 is shown as a side view, and in FIG. 6C, there is shown a detail view of the teeth. Identical descriptions apply to the 7 mm×11 mm×11 mm views of the implants of FIGS. 6D–6F and the 7 mm×14 mm×14 mm implant of FIGS. 6G–6I.

Figure 7A:
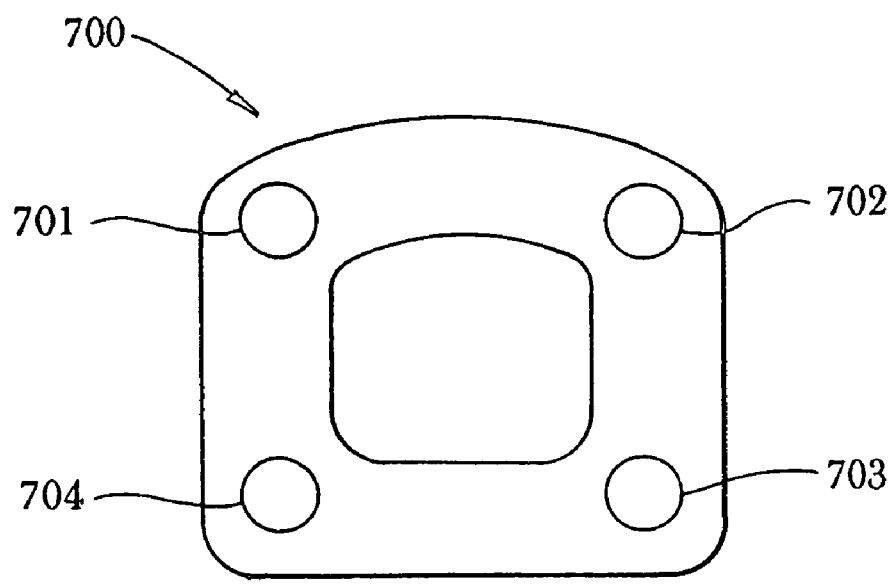
Figure 7B:
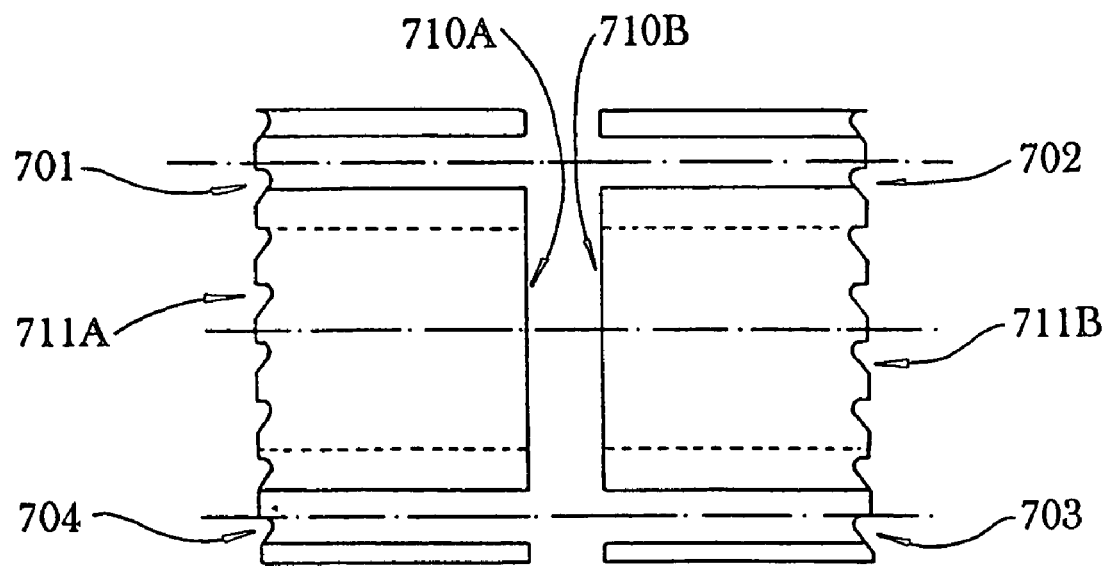
Figure 9:
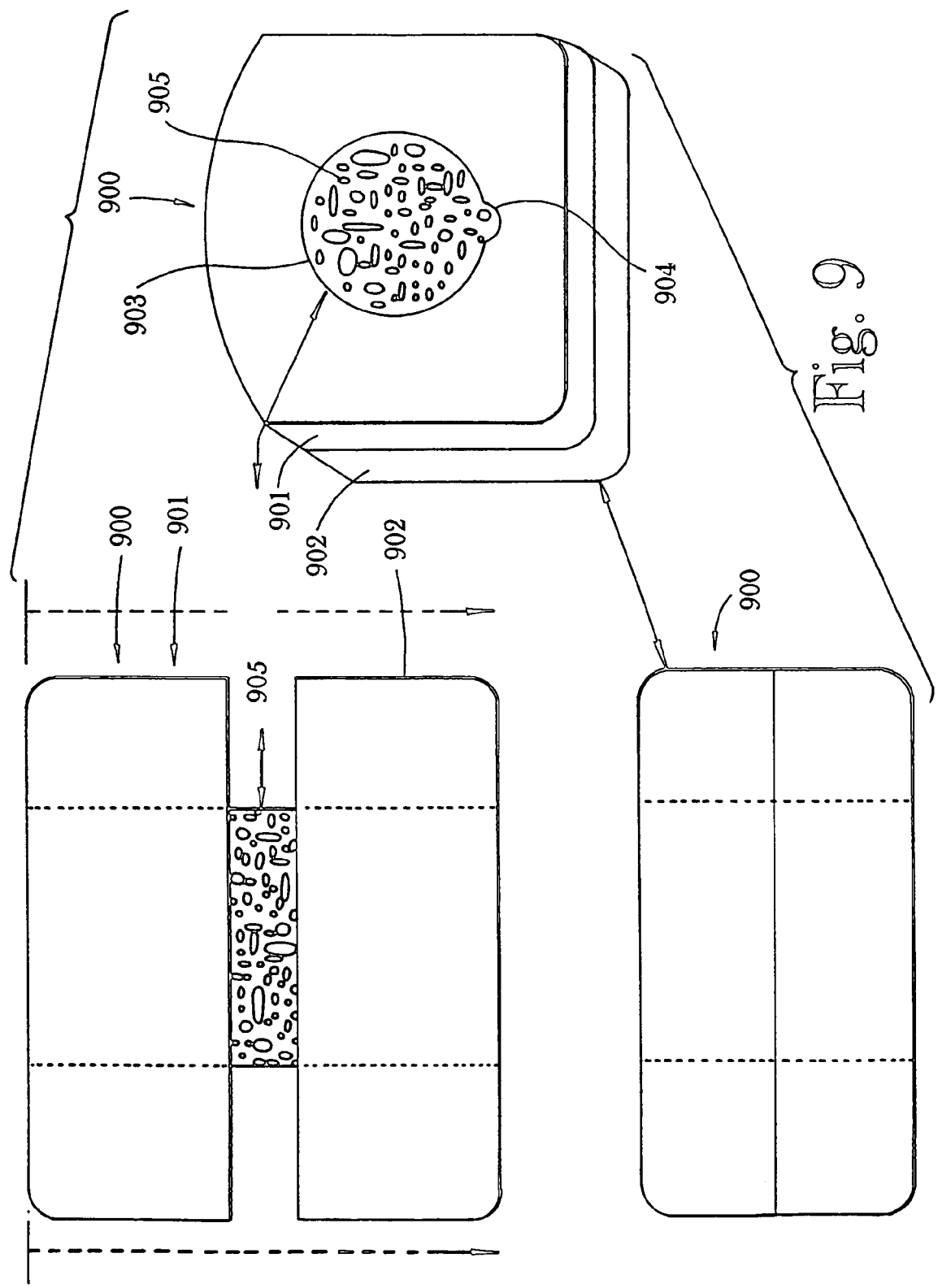

In FIG. 7, there is shown a further aspect of this invention in which an implant, either machined as described above, or prior to said machining, is further machined so as to allow stacking thereof to achieve implants of various heights. Commencing from a blank cortical plug at the stage shown in FIG. 2D has the advantage that if breakage of the implant occurs during machining, this will likely occur prior to completion of all of machining steps. According to this embodiment of the invention, two implant blanks of known height are selected such that a unitary implant composed of both starting implants can be produced of a new desired height (e.g. a 6 mm high implant may be stacked with a 7 mm high implant to produce a 13 mm implant). Each implant blank is placed in a drill jig, and by means of a drill press or like means, holes are drilled through the implants. With the implants still in the jig, the jig is placed on the table of an arbor press. Pins, composed of cortical bone, resorbable but strong biocompatible synthetic material, or metallic pins of the appropriate diameter are then impelled into the holes in the implants such that the implants are formed into a unitary body by these pins. In order to encourage bony ingrowth, channels may be cut into the adjacent surfaces of the implants. The embodiment shown in FIG. 7A is a top view of an implant 700 into which four holes 701–704 have been drilled. In FIG. 7B, there is shown the juxtaposition of two implants 700A and 700B, with the drilled holes 701–704 in register to receive pins for maintaining the implants in register. In this view, the adjacent surfaces 710A and 710B have not been inscribed with teeth, while the surfaces 711A and 711B have been so inscribed. Based on this disclosure, those skilled in the art will recognize that a number of variations and modifications may be made to stack various forms of bone implants, or to maintain such implants in register with each other. These modifications are to be considered within the scope of this invention. Thus, as shown in FIG. 9, an implant 900 is produced by producing two implants 901 and 902, each having a cavity or canal 903, including an asymmetric key way 904 machined therein. By press-fitting the two implants together using an appropriately shaped cancellous plug 905 or a plug made from another biocompatible material, including but not limited to hydroxyapatite, cortical bone, synthetic materials, ceramic, optionally treated with growth factors such as bone morphogenetic protein and the like, the two implants 901 and 902 are retained in registered juxtaposition to form the implant 900.

In a further embodiment of this invention, shown in FIG. 8, a method for assembling the implant of this invention from component parts is provided. In FIG. 8A, there is shown an implant 800 composed of two side-by-side halves, 801A and 801B. The two halves of the implant are brought into juxtaposition to form a unitary implant. The two halves may be implanted in juxtaposition, or holes may be formed in each half, and the halves maintained in contact by forcing pins through the holes, in a fashion analogous to that described above for maintaining stacked implants in contact with each other. For this embodiment of the invention, a portion of cortical bone may be harvested from any suitable source of cortical bone. As shown in FIG. 8B, a segment, in the form of a block or a column of cortical bone is harvested along the long axis of a long bone, such as the femur, tibia, or fibula. The shape of the bone may be inscribed into the thus-harvested cortical bone by routing, broaching or other means as described herein. The thus-machined cortical bone may then be sectioned into appropriate heights, as needed, to provide the implant halves 801A and 801B. Alternate sites for harvesting the cortical bone segment are shown in FIGS. 8B and 8C.

Figure 8F:
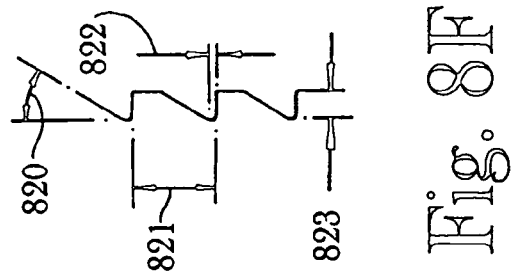
Figure 8E:
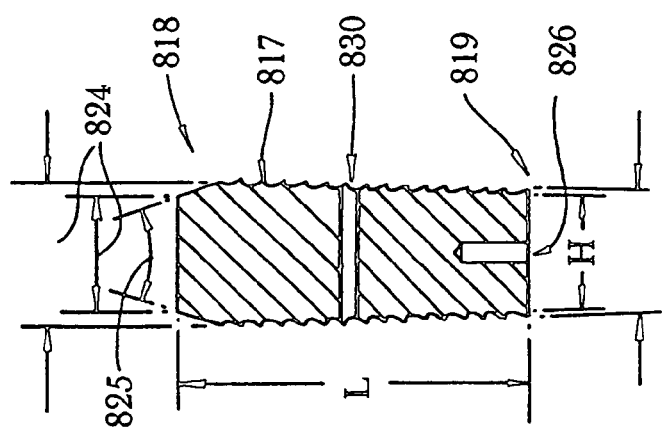
Figure 8G:
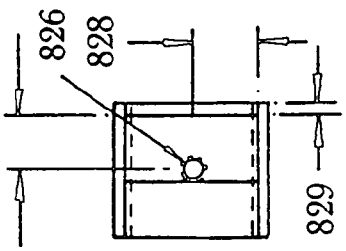
Figure 8D:
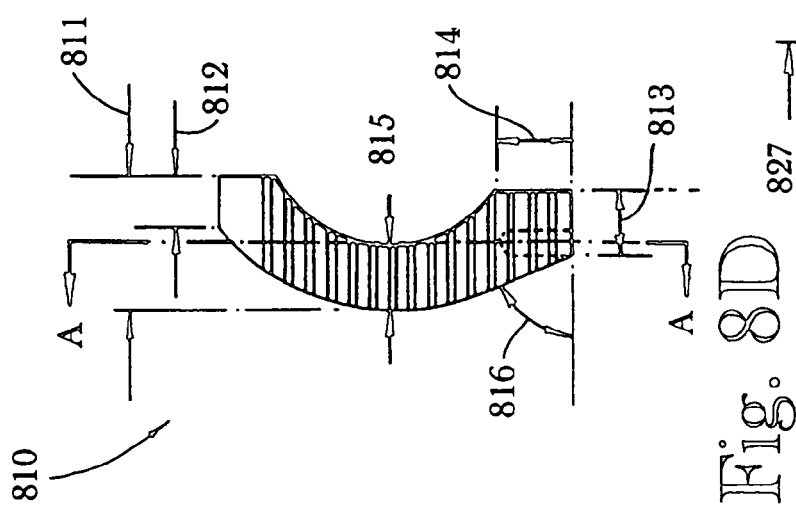

In addition to use for cervical Smith-Robinson type fusion, implants comprising each element, 801A or 801B alone, modifications and variations thereof, optionally in combination with another vertebral fusion implant, may be implanted, for example, to assist in induction of posterior lumbar intervertebral fusion (PLIF). In such a case, a device 810, such as that shown in FIGS. 8D–8G is machined from bone stock as shown in FIGS. 8B, 8C or another appropriate bone stock, and is inserted, according to methods known in the art for insertion of PLIF implants. Preferably, the device as used for PLIF applications has the following dimensions similar to the following, see side view FIG. 8D: a width 811 of approximately 7 to 12 mm, and preferably about 9.4 to about 10 mm; a top dimension 812 of about 4 to 5 mm; a bottom dimension 813 of about 4–6 mm and preferably about 5 mm; a flat surface of 814 of about 4–7 mm, and preferably about 5.5 mm; a width 815 of about 5–7 mm and preferably about 5 mm; a curvature that defines an angle 816 of between about 60 and 75 degrees, and preferably about 67 degrees. See FIG. 8E, rear view: a length L of about 20 to 26 mm; a height H of between about 7.5 and 14.5 mm; preferably, heights of about 8, 10, 12, and 14 mm are produced with lengths of about 20 and 26 mm; desirably, the side faces 817 are machined to display a rough, ridged or grooved surface so that when the anterior end 818 of the PLIF implant is properly seated in place, ridges directed to the posterior end 819 of the PLIF implant prevent backing out of the implant. A detail of one embodiment of such a ridged surface is shown in FIG. 8F, wherein the following dimensions are preferred: an angle 820 for each tooth of between about 30 and 40 degrees, preferably about 35 degrees; a distance between tooth crests 821 of about 1–2 mm, preferably about 1.5 mm; a tooth crest width 822 of about 0.1 to about 0.2 mm, preferably about 0.125 mm; and a tooth height 823 of between about 0.1 to about 1 mm and preferably about 0.5 mm; returning to FIG. 8E, the implant preferably has an anterior end width 824 of about 7–13 mm, preferably about 9–13 mm, with a taper angle 825 from the height H of about 30 to 40 degrees, preferably about 35 degrees; an instrument attachment means, 826, such as a tapped instrument attachment hole, is provided in the posterior face of the PLIF implant; this feature is best seen from the posterior view 8G, which shows: an instrument attachment hole 826 having a diameter of about 1.5 to about 2.5 mm, preferably about 2 mm, and a depth of about 4–5 mm, preferably about 4.5 mm; an edge to center of the instrument attachment hole dimension 827 is carefully defined to match dimensions of any implant insertion device used in combination with this embodiment of the PLIF implant; a center of the instrument attachment hole to edge dimension 828 is about 4–6 mm, preferably about 5 mm, with a ridge 829 of about 1 mm running along three edges of the posterior face of the implant. In displaying the section A—A from FIG. 8D in FIG. 8E, a slight air gap 830 is shown as the section would exit bone on the concave surface of the implant and then reenter bone.

In use, the implant 810 is inserted on either side of lumbar intervertebral spaces to thereby stabilize and assist in fusion of adjacent lumbar vertebrae. This is accomplished by distraction of the lumbar vertebrae, removal of an appropriate amount and shape of intervertebral disc matter, and insertion of the implant 810, preferably on each side on a posterior approach, according to methods known in the art. The concave surface of each implant 810 is set to face inwardly, toward the center of the vertebral body, while the convex surface of the implant 810 is set to match, as much as possible, the natural external curvature of the lumbar vertebrae.

Figure 10A:
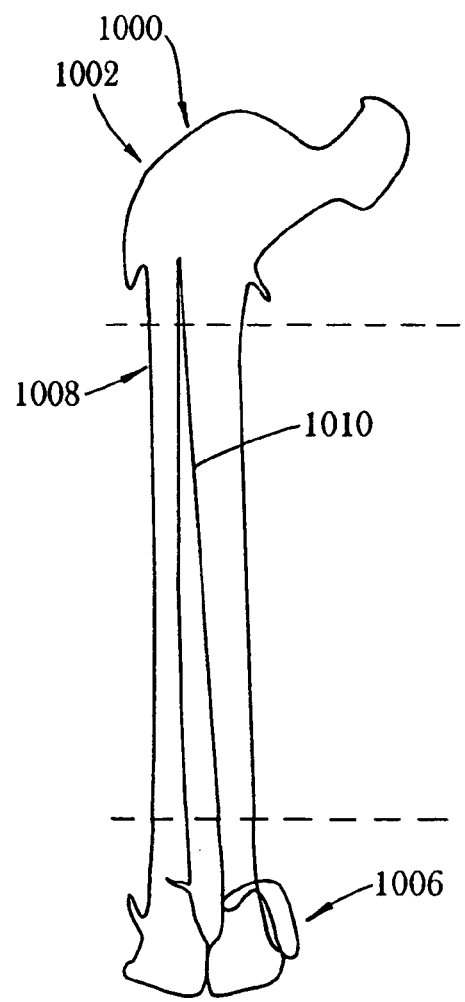
FIG. 10 shows an alternate method for producing bone stock for making the implant of this invention of essentially unlimited height from the anterior margin of the tibia or the linea aspera of the femur.
Figure 10B:
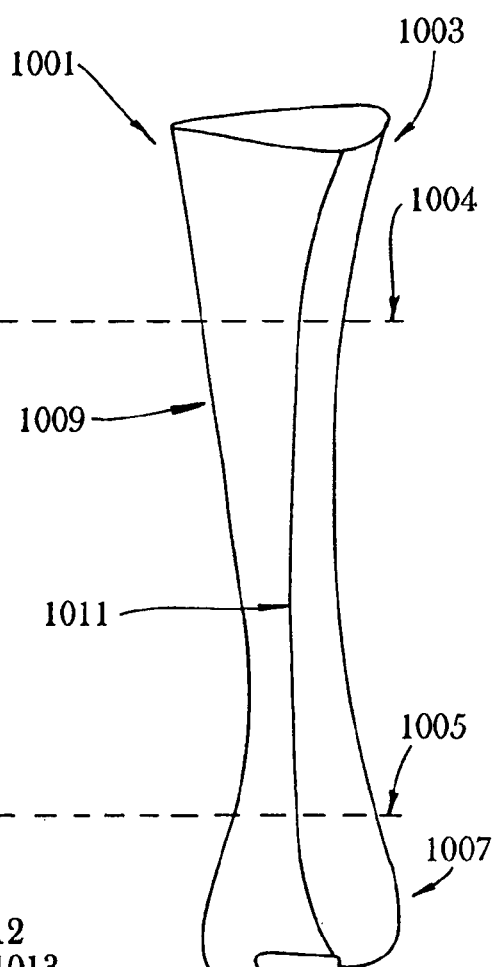
Figure 10C:
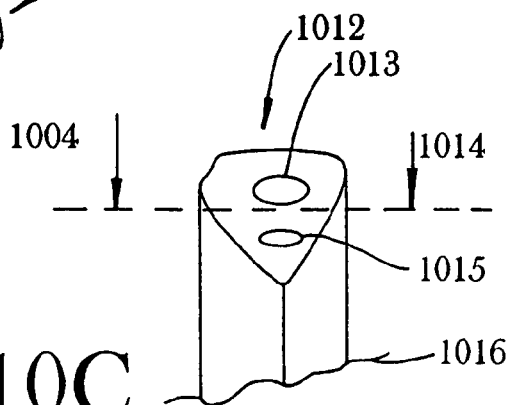

In an analogous but alternate method for production of the cervical implant, unitary implants may be produced by appropriately sectioning and machining the anterior margin of the tibia or linea aspera of the femur. Thus, as shown in FIG. 10A, a left femur 1000 (posterior aspect), or in FIG. 10B, a left tibia 1001 (anterior aspect), is sectioned at 1004 and 1005 to remove the head, neck and greater trochanter 1002 and internal and internal condyles 1006 of the femur, or tubercle and tuberosity 1003 malleolus 1007 of the tibia. The result from such sectioning is the production of a shaft, or diaphysis, of the femur 1008 or tibia 1009. Further processing according to this aspect of the invention involves the line asper 1010 of the femur or the anterior margin of the tibia 1011, as shown in FIG. 10C. Whether produced from the femur or tibia, a diaphysial shaft 1012, extending as shown at 1016 to a length permitted by the length of the shaft produced by the sectioning at 1004/1005. The shaft comprises the natural intramedullary canal 1013. The thus produced shaft is then further sectioned in a plane shown at 1014 to produce a shaft of bone removed from the natural intramedullary canal 1013 having a cylindrical but somewhat triangular external shape. Into this shaft may be drilled a cannulation 1015, as shown in FIG. 11.

Figure 11:
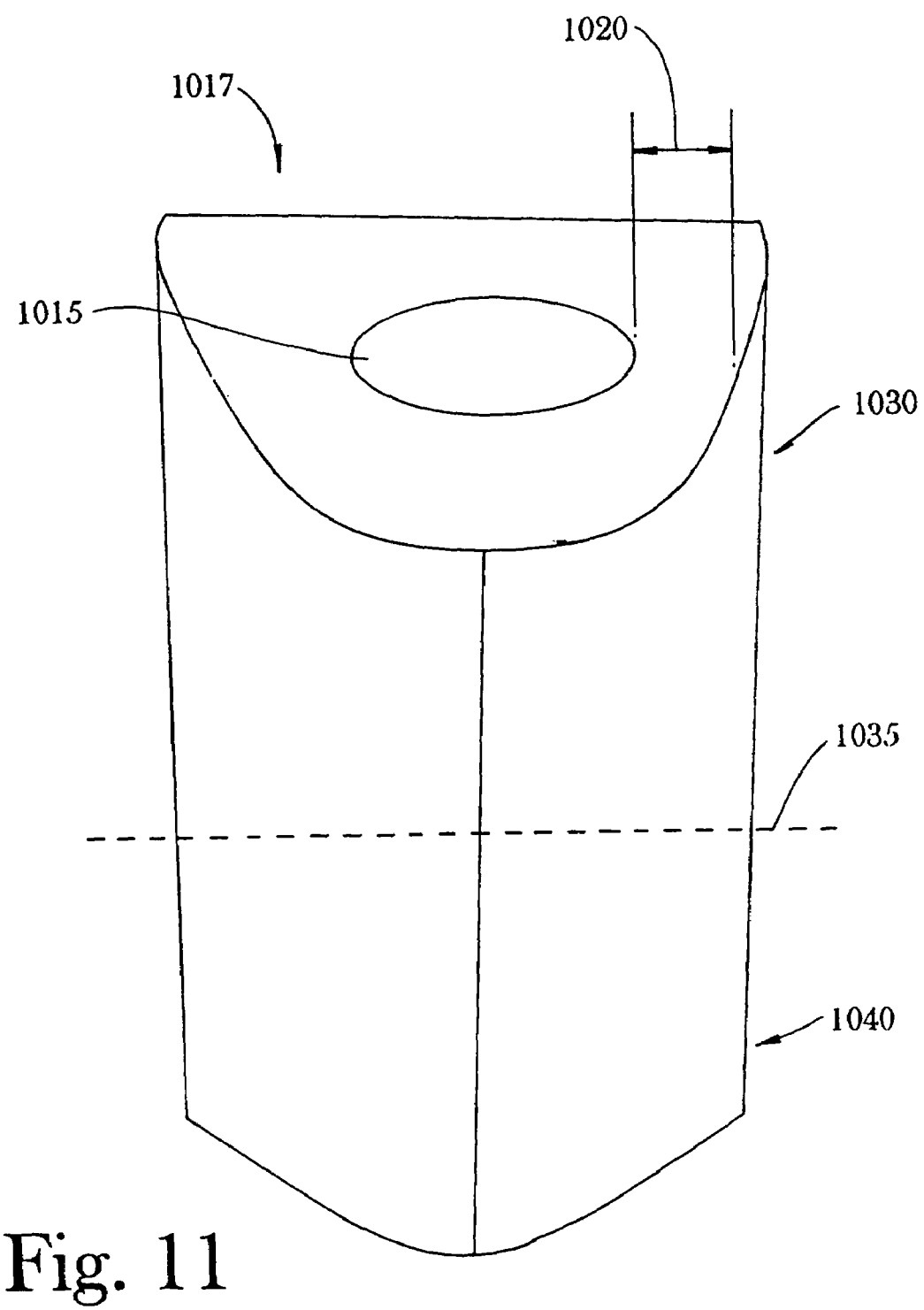
FIG. 11 shows dimensions and further processing of the implant of this invention produced according to the alternate method of FIG. 10.
Figure 12C:
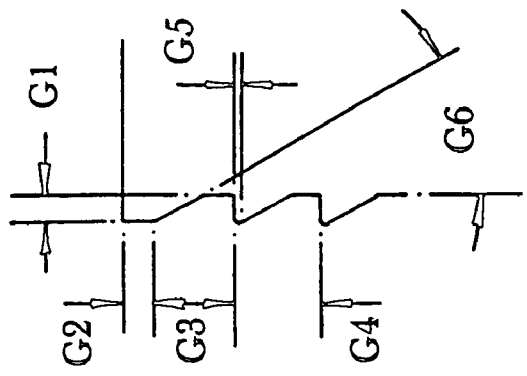
Figure 12B:
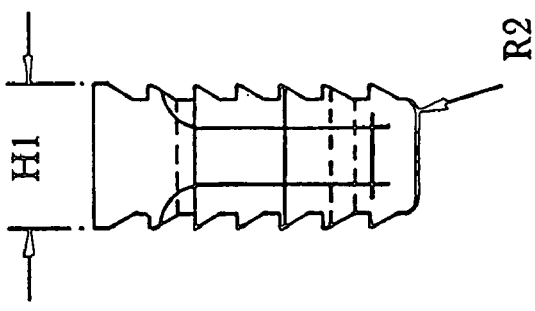
Figure 12A:
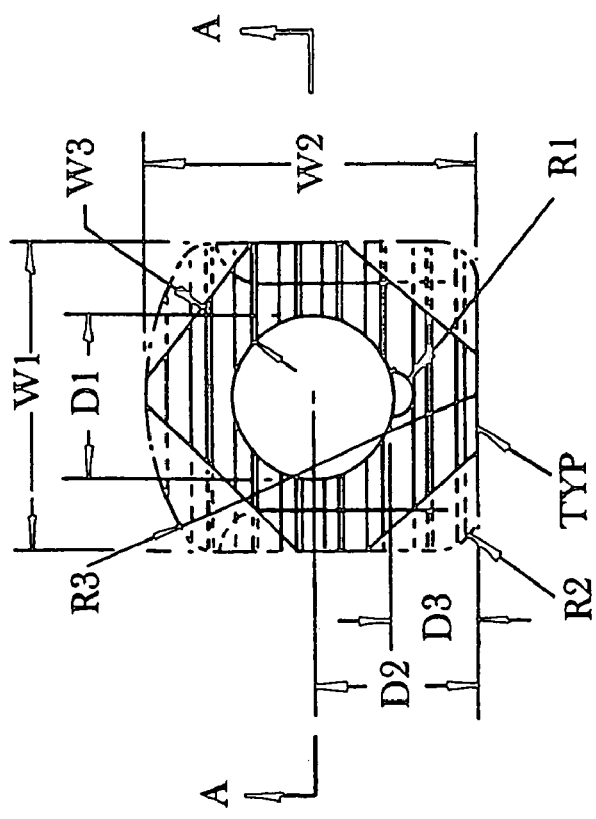
Figure 12D:
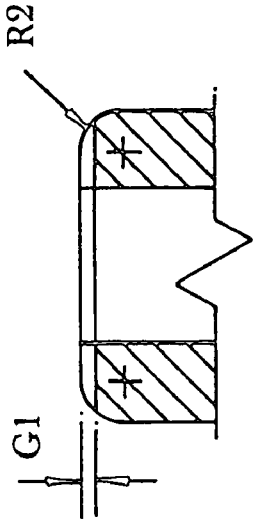
Figure 14C:
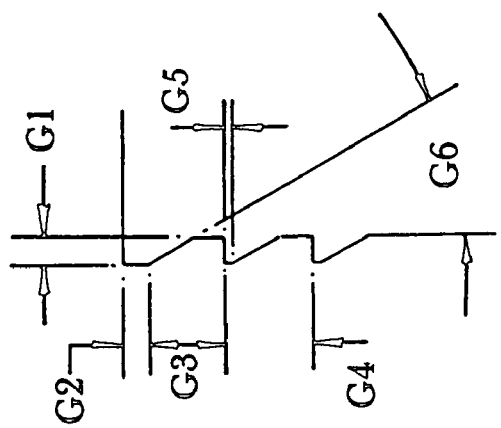
Figure 14B:
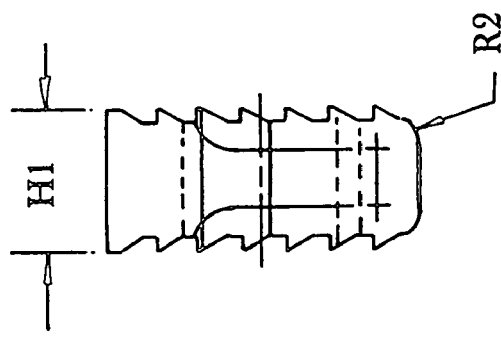
Figure 14A:
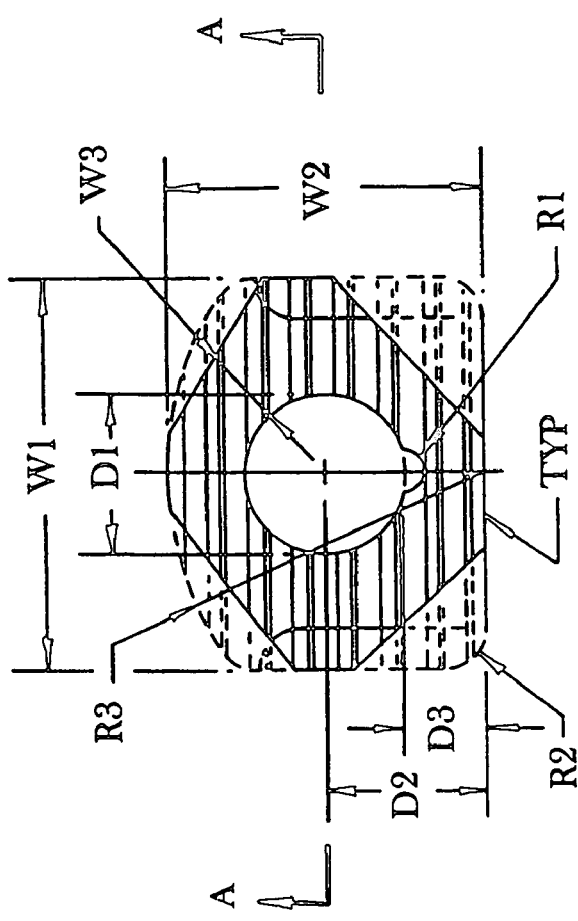
Figure 14D:
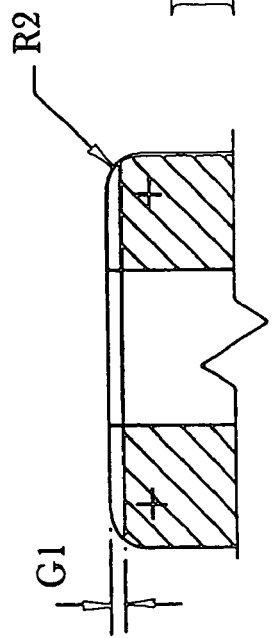
Figure 15C:
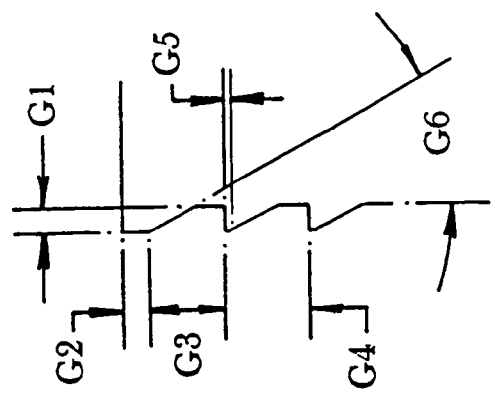
Figure 15B:
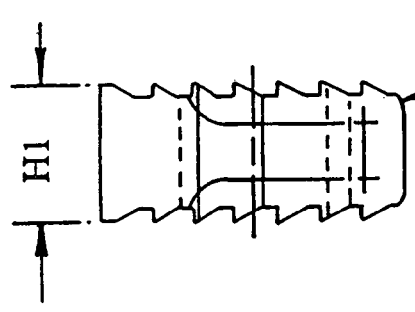
Figure 15F:
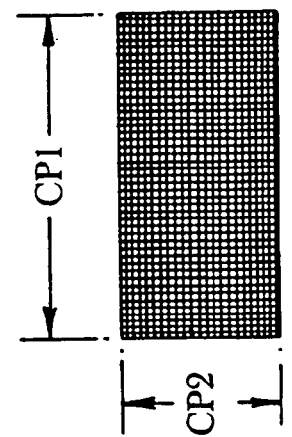
Figure 15A:
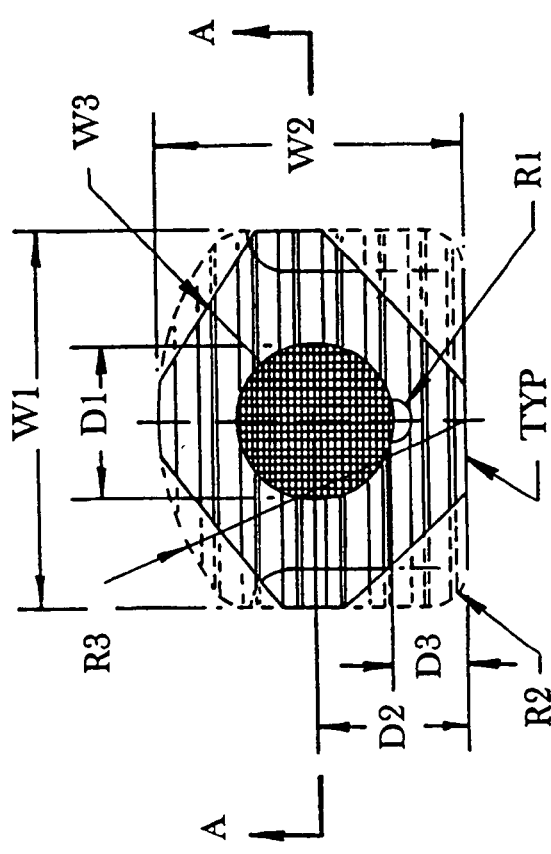
Figures 15D, 15E:
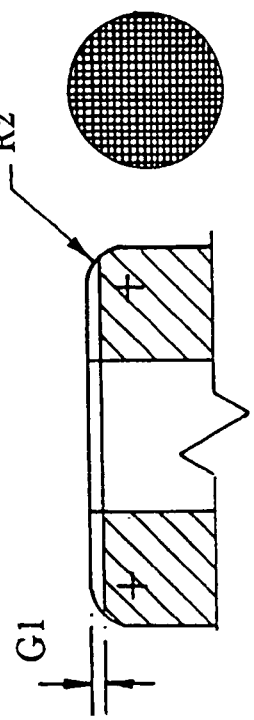

FIG. 11 shows the substantially triangular shaft of substantially cortical bone 1017 produced by sectioning the shaft of the long bone down the plane 1014. Into the shaft of bone 1017 may be drilled a bore to produce a cannulation 1015 of appropriate dimensions. The cannulation 1015 may be introduced into the unitary shaft of bone 1017 or it may be introduced into sub-segments thereof by first cutting the shaft 1017 at 1035. In either case, the diameter of the cannulation 1015 should be limited such that at the narrowest portion between the cannulation and the wall of the device 1020 never falls below about 2 mm. When sectioned at 1035, for example by mounting the shaft 1017 on a lathe and contacting the spinning shaft with a very narrow blade (i.e. a parting tool of about 1 mm or less width), implant blanks 1030 and 1040 are produced which may be further machined to achieve desired external and internal profiles and key way features, as described for the implant of this invention produced by alternate methods described hereinabove. Implants of any desired height, for example 5 mm to about 14 mm, may thus be produced. FIGS. 12–17 show specific embodiments of the implant of this invention produced according to this aspect of the invention.

Per FIGS. 12–17, there is provided views of five different cortical bone implants according to this invention having particular geometries by way of example and not limitation. In each figure, view A is a top view, view B is a side view, view C is a detail of the grooves which angle toward the posterior aspect of the implant, and view D is a sectional view through the line A—A shown in view A. In addition, where an osteogenic plug, such as a cancellous plug is present, this is shown in view E as a top view and view F as a side view of the cancellous plug. In FIG. 12, there is shown an example of an implant having a height H1 between about 5 mm and about 9 mm, a width W1 of about 11 mm, and a width W2 of about 11 mm. An outer dotted profile provides a means for comparing the shape of the implant produced according to this alternate manufacturing method with the external profile of the implant of FIG. 6. As can be seen, the implant produced according to this aspect of the invention has a substantially diamond-shaped external profile, as a result of the geometry of the starting shaft 1017 of bone stock.

FIG. 13 shows a device similar to that of FIG. 12, with a cancellous plug inserted therein. FIG. 14 shows a device having a width W1 of about 14 mm and a height H1 of between about 5 mm and about 14 mm. FIG. 15 shows a device similar to that of FIG. 14 with a cancellous plug inserted therein. FIG. 16 shows a device having a width W1 of about 14 mm, a width W2 of about 14 mm, and a height of between about 5 mm and II mm. FIG. 17 shows a device similar to that of FIG. 16 having a cancellous plug inserted therein. Table I below summarizes the various features and provides examples of specific dimensions for various embodiments of the implant of this invention shown in FIGS. 12–17:

4.4 Manner of Using the Implant

In use, the implant 100 is inserted into a space formed between adjacent vertebrae that are required to be fused. This may be accomplished by the surgeon removing portions of the intervertebral disk, (partial discectomy) and retracting the adjacent vertebrae to allow insertion of an appropriately dimensioned implant. The rear end 105 of the implant is inserted first, and where present, the external feature 120 prevents backing out of the implant. Where no external feature 120 has been inscribed into the top and bottom surfaces of the implant, it may be necessary to affix the implant in position with plate and screw retention systems known in the art. According to this invention, implants are provided having a height of between about 7 and 14 mm, a length of between about 11 and 14 mm and a width of between about 11 and 14 mm. Any permutation or combination of these dimensions may be envisioned, for example (in order of height, length, width): 7×11×11, 8×11×11, etc.; 7×14×14, 8×14×14, etc.; 7×11×14, 8×11×14, etc.

Preferably, the surgeon performing the implantation saves the autologous material and debris produced in the course of the partial discectomy for packing into the canal of the present implant. In addition, or alternatively, the canal may be packed (either during the surgical procedure or the canal may be pre-packed) with osteogenic, osteoinductive, or osteoconductive materials, including but not limited to: allograft bone, autograft bone, autogenous osteogenic materials including bone marrow cancellous bone and the like, demineralized bone, freeze-dried demineralized bone, Grafton® (demineralized bone in glycerol), bone powder, bone derivatives, bone morphogenetic protein (purified or recombinant), antibiotic, bioactive glass, hyrdorxyapatite, bioactive ceramics, or combinations thereof.

Following implantation, the recipient (whether human or animal) is monitored for implant stability and success in fusion. Fusion is achieved over the course of several weeks to several months, during which time increasing levels of load may be placed on the spine.

TABLE I

| Code | Description | Figure # | | | | | |
|---|---|---|---|---|---|---|---|
| | | 12 | 13 | 14 | 15 | 16 | 17 |
| D1 | Inner Hole Diameter | 5.5 | 5.5 | 5.5 | 5.5 | 5.5 | 5.5 |
| D2 | Hole Centerline Distance | 5.5 | 5.5 | 5.5 | 5.5 | 5.5 | 5.5 |
| D3 | Key Way Centerline Distance | 2.9 | 2.9 | 2.9 | 2.9 | 4.4 | 4.4 |
| G1 | Groove Depth | 0.5 | 0.5 | 0.5 | 0.5 | 0.5 | 0.5 |
| G2 | Top Flat Width | 0.5 | 0.5 | 0.5 | 0.5 | 0.5 | 0.5 |
| G3 | Groove Pitch width without G5 | 1.375 | 1.375 | 1.375 | 1.375 | 1.375 | 1.375 |
| G4 | Groove Pitch width with G5 | 1.5 | 1.5 | 1.5 | 1.5 | 1.5 | 1.5 |
| G5 | Flat Width | 0.125 | 0.125 | 0.125 | 0.125 | 0.125 | 0.125 |
| G6 | Groove Angle (degrees) | 30 | 30 | 30 | 30 | 30 | 30 |
| H1 | Overall Height | 5–9 | 5–9 | 5–13 | 5–13 | 5–11 | 5–11 |
| R1 | Keyway Radius | 0.8 | 0.8 | 0.8 | 0.8 | 0.8 | 0.8 |
| R2 | Corner Radius | 1.5 | 1.5 | 1.5 | 1.5 | 1.5 | 1.5 |
| R3 | Outside Arch Radius | 11 | 11 | 11 | 11 | 14 | 14 |
| W1 | Outside Width | 11 | 11 | 14 | 14 | 14 | 14 |
| W2 | Outside Width | 11 | 11 | 11 | 11 | 14 | 14 |
| W3 | Wall Thickness | ^2 | ^2 | ^2 | ^2 | ^2 | ^2 |
| CP1 | Cancellous Plug Height | N/A | 5–9 | N/A | 5–13 | N/A | 5–11 |
| CP2 | Cancellous Plug Diameter | N/A | 5.7–5.8 | N/A | 5.7–5.8 | N/A | 5.7–5.8 |

5.0 REFERENCES

Bailey, R. W., and Badgley, L. E. (1960) *Stabilization of the Cervical Spine by Anterior Fusion*, J. Bone and Joint Surg. 42A:565–594.

Cloward, R B. (1958) *The Anterior Approach for Removal of Ruptured Cervical Discs*, J. Bone and Joint Surg. 15:602–617.

Grooms et al., (1996) *Success of Surgery on the Anterior Cervical Spine: Smith-Robinson Technique vs. Internal Plates*, Clinical Performance of Skeletal Prostheses, L. L. Hench and J. Wilson, Eds., Chapman & Hall.

Robinson, R. A., et al., (1962) *The Results of Anterior Interbody Fusion of the Cervical Spine*, J. Bone and Joint Surg. 44A: 1569–1587.

Robinson, R. A. and Smith, G. W. (1955) *Anterolateral Cervical Disc Removal and Interbody Fusion for Cervical Disc Syndrome*, Bull. Johns Hopkins Hosp. 96:223–224.

Smith, G. W. and Robinson, R. A., (1958), *The Treatment of Certain Cervical-Spine Disorders by Anterior Removal of the Intervertebral Disc and Interbody Fusion*, J. Bone and Joint Surg. 40A:607–623.

White, A. A. III, and Hirsh, C. (1972) *An Experimental Study of the Immediate Load Bearing Capacity of Some Commonly Used Iliac Bone Grafts*, Acta Orthop. Scandanav. 42:482–490.

Whitecloud, T. S. III and Dunsker, S. (1993) *Anterior Cervical Spine Surgery, Principles and Techniques in Spine Surgery*, Raven Press, N.Y.

U.S. Pat. No. 5,306,309
U.S. Pat. No. 5,609,635
U.S. Pat. No. 5,306,307
U.S. Pat. No. 4,950,296

What is claimed is:

1. An elongated bone implant for use in lumbar spinal fusions, said elongated bone implant having a length of 20 mm to 26 mm, an overall width of approximately 7 mm to 12 mm and a height of between about 7.5 mm and 14.5 mm, said elongated bone implant comprising a section of bone that comprises a substantially planar upper surface and a substantially planar lower surface that is opposite said substantially planar upper surface, an anterior end and a posterior end opposite said anterior end, a first outer side wall extending the length of said implant and a second outer side wall opposite said first outer side wall, wherein said first outer side wall and said second outer side wall extend between said substantially planar upper surface and said substantially planar lower surface, and wherein said second outer side wall comprises either a concave surface or both linear and concave surfaces, said first outer side wall and said second outer side wall being elongated relative to said anterior end and said posterior end, said elongated implant being free of an intermedullary canal as a transverse cavity through the body of said elongated implant.

2. The elongated bone implant of claim 1, wherein said first outer side wall comprises a convex surface.

3. The elongated bone implant of claim 1, wherein said elongated bone implant comprises autograft or allograft cortical or cancellous bone.

4. The elongated bone implant of claim 1, wherein said substantially planar upper surface, said substantially planar lower surface, or both are machined to display a rough, ridged or grooved surface to aid in preventing said bone implant from moving out of place.

5. The elongated bone implant of claim 1, wherein said substantially planar upper surface and said substantially planar lower surface are machined to display ridges that are configured to prevent said bone implant from sliding back toward the direction from which said bone implant is inserted.

6. A method of fusing a first lumbar vertebra to a second lumbar vertebra comprising distracting said first and second lumbar vertebrae; removing a portion of an intervertebral disc positioned between said first and second lumbar vertebrae thereby creating a space, and implanting an elongated bone implant according to claim 1 into said space, wherein said elongated bone implant is positioned such that said second outer side wall having said concave surface faces inwardly.

7. The elongated implant of claim 1, wherein the overall width is from about 9.4 mm to about 10 mm.

8. An elongated bone implant for use in lumbar spinal fusions, said elongated bone implant having a length of 20 mm to 26 mm, an overall width of approximately 7 mm to 12 mm and a height of between about 7.5 mm and 14.5 mm, said elongated bone implant comprising a section of bone that comprises a substantially planar upper surface and a substantially planar lower surface that is opposite said substantially planar upper surface, an anterior face and a posterior face opposite said anterior face, a first outer side wall extending the length of said implant and a second outer side wall opposite said first outer side wall, wherein said first outer side wall and said second outer side wall extend between said substantially planar upper surface and said substantially planar lower surface, and wherein said second outer side wall comprises a concave surface.

9. The elongated implant of claim 8, wherein the overall width is from about 9.4 mm to about 10 mm.

10. The elongated implant of claim 8, wherein the height of said elongated implant is about 8 mm.

11. The elongated implant of claim 8, wherein the height of said elongated implant is about 10 mm.

12. The elongated implant of claim 8, wherein the height of said elongated implant is about 12 mm.

13. The elongated implant of claim 8, wherein the height of said elongated implant is about 14 mm.

14. The elongated implant of claim 8, wherein the substantially planar upper surface or substantially planar lower surface is machined so that it has ridges directed to the posterior end of the implant.

15. The elongated implant of claim 14 wherein the distances between tooth crests in said ridges is about 1 to 2 mm.

16. The elongated implant of claim 8 wherein said posterior face is machined for instrument attachment.

17. The elongated implant of claim 16 wherein said posterior face has an instrument attachment hole.

18. The elongated implant of claim 17 wherein said instrument attachment hole is a tapped instrument attachment hole.

19. An elongated bone implant for use in lumbar spinal fusions, said elongated bone implant having a length of 20 mm to 26 mm, an overall width of approximately 7 mm to 12 mm, a height of between about 7.5 mm and 14.5 mm, said elongated bone implant comprising a section of bone that comprises a substantially planar upper surface and a substantially planar lower surface that is opposite said substantially planar upper surface, an anterior end and a posterior end opposite said anterior end, a first outer side wall extending the length of said implant and a second outer side wall opposite said first outer side wall, wherein said first outer side wall and said second outer side wall extend between said substantially planar upper surface and said substantially planar lower surface, and wherein said first outer side wall comprises a convex surface and defines an outside angle of between about 60° and 75° with said posterior end, said second outer side wall comprises a concave surface.

20. The elongated implant of claim 19, wherein the overall width is from about 9.4 mm to about 10 mm.

21. The elongated implant of claim 19, wherein the height of said elongated implant is about 8 mm.

22. The elongated implant of claim 19, wherein the height of said elongated implant is about 10 mm.

23. The elongated implant of claim 19, wherein the height of said elongated implant is about 12 mm.

24. The elongated implant of claim 19, wherein the height of said elongated implant is about 14 mm.

25. The elongated implant of claim 19, wherein said outside angle is about 67°.

26. The elongated implant of claim 19, wherein the substantially planar upper surface or substantially planar lower surface is machined so that it has ridges directed to the posterior end of the implant.

27. The elongated implant of claim 26 wherein the distances between tooth crests in said ridges is about 1 to 2 mm.

28. The elongated implant of claim 19 wherein said posterior face is machined for instrument attachment.

29. The elongated implant of claim 28 wherein said posterior face has an instrument attachment hole.

30. The elongated implant of claim 29 wherein said instrument attachment hole is a tapped instrument attachment hole.

31. An elongated bone implant for use in lumbar spinal fusions, said elongated bone implant being crescent shaped and having a length of 20 mm to 26 mm, an overall width of approximately 7 mm to 12 mm, a height of between about 7.5 mm and 14.5 mm, said elongated bone implant comprising a section of bone that comprises a substantially planar upper surface and a substantially planar lower surface that is opposite said substantially planar upper surface, an anterior end and a posterior end opposite said anterior end, a first outer side wall extending the length of said implant and a second outer side wall opposite said first outer side wall, wherein said first outer side wall and said second outer side wall extend between said substantially planar upper surface and said substantially planar lower surface, and wherein said first outer side wall comprises a convex surface and defines an outside angle of between about 60° and 75° with said posterior end, said second outer side wall comprises a concave surface.

* * * * *